US009410206B2

(12) United States Patent
Hoon et al.

(10) Patent No.: US 9,410,206 B2
(45) Date of Patent: Aug. 9, 2016

(54) LONG NONCODING RNA (LNCRNA) AS A BIOMARKER AND THERAPEUTIC MARKER IN CANCER

(71) Applicants: Dave S. B. Hoon, Santa Monica, CA (US); Laurent Lessard, Santa Monica, CA (US)

(72) Inventors: Dave S. B. Hoon, Santa Monica, CA (US); Laurent Lessard, Santa Monica, CA (US)

(73) Assignee: JOHN WAYNE CANCER INSTITUTE, Santa Monica, CA (US)

( * ) Notice: Subject to any disclaimer, the term of this patent is extended or adjusted under 35 U.S.C. 154(b) by 216 days.

(21) Appl. No.: 13/691,716

(22) Filed: Nov. 30, 2012

(65) Prior Publication Data

US 2013/0178428 A1 Jul. 11, 2013

Related U.S. Application Data

(60) Provisional application No. 61/565,424, filed on Nov. 30, 2011.

(51) Int. Cl.
*C12Q 1/68* (2006.01)

(52) U.S. Cl.
CPC ........ *C12Q 1/6886* (2013.01); *C12Q 2600/112* (2013.01); *C12Q 2600/118* (2013.01); *C12Q 2600/154* (2013.01); *C12Q 2600/156* (2013.01); *C12Q 2600/158* (2013.01)

(58) Field of Classification Search
USPC ........................ 435/6.1, 6.12, 6.14, 91.1, 375
See application file for complete search history.

(56) References Cited

FOREIGN PATENT DOCUMENTS

WO WO2009046118 A1 4/2009

OTHER PUBLICATIONS

ClinicalTrials.gov. ClinicalTrials.gov, Identifier NCT00899574. Imiquimod for Breast Cancer Patients With Chest Wall Recurrence or Skin Metastases. Downloaded on Nov. 18, 2015 from https://clinicaltrials.gov/ct2/show/NCT00899574.*

Gibb, et al., "The functional role of non-coding RNA in human carcinomas", Molecular Cancer 10, 2011, 38.

Jia, et al., "N6-methyladenosine in nuclear RNA is a major substrate of the obesity-associated FTO", Nature Chem Biol Oct. 7, 2011, 885-7.

Maris, et al., "Chromosome 6p22 locus associated with clinically aggressive neuroblastoma", NEJM 358 Jun. 2008, 2585-93.

Motorin, et al., "5-methylcytosine in RNA: Detection, enzymatic formation and biological functions", Nucleic Acids Res 38 2010, 1415-30.

Presner, et al., "The emergence of lncRNAs in cancer biology", Cancer Discovery Oct. 1, 2011, 391-407.

Ryan, et al., "Genetic varation in microRNA networks: The implications for cancer research", Nature Cancer Reviews Jul. 10, 2010, 389-402.

Verhaegh, et al., "Polymorphisms in the H19 gene and the risk of bladder cancer", European Urology 54 Feb. 2008, 1118-26.

Wang, et al., "Molecular mechanisms of long noncoding RNAs", Molecular Cell vol. 42 Sep. 2011, 904-14.

* cited by examiner

*Primary Examiner* — Terra C Gibbs
(74) *Attorney, Agent, or Firm* — Perkins Coie LLP

(57) ABSTRACT

Long noncoding RNAs (lncRNAs) that may be used as cancer biomarkers and methods of diagnosing, prognosing and monitoring cancer including, but not limited to, cutaneous melanoma using said lncRNAs are provided herein. In some embodiments, the methods include steps of isolating one or more lncRNA transcripts in a biological sample from the subject; measuring a test level of the one or more isolated lncRNA transcripts; comparing the test level to a control level of the one or more lncRNA transcripts; and diagnosing or making a prognosis based on the lncRNA level. In some embodiments, the lncRNA transcript is an linc00340 transcript or variant thereof. These lncRNA transcripts may also be used as a therapeutic target in the treatment of cancer.

13 Claims, 16 Drawing Sheets

FIGURE 4
A.
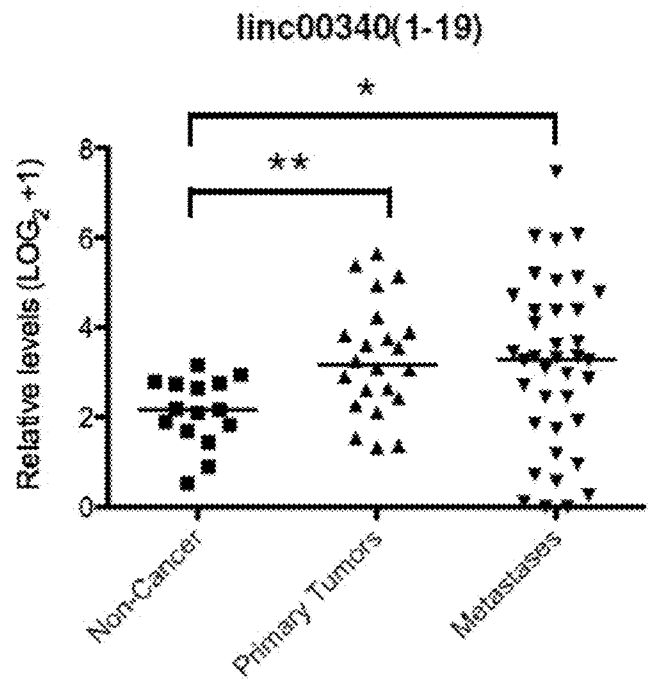
B.
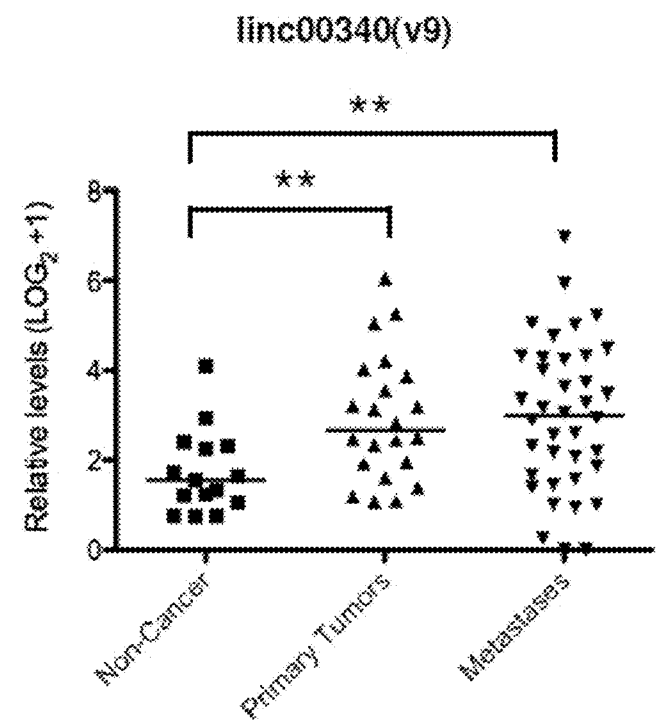

FIGURE 6
A. linc00340(1-19)
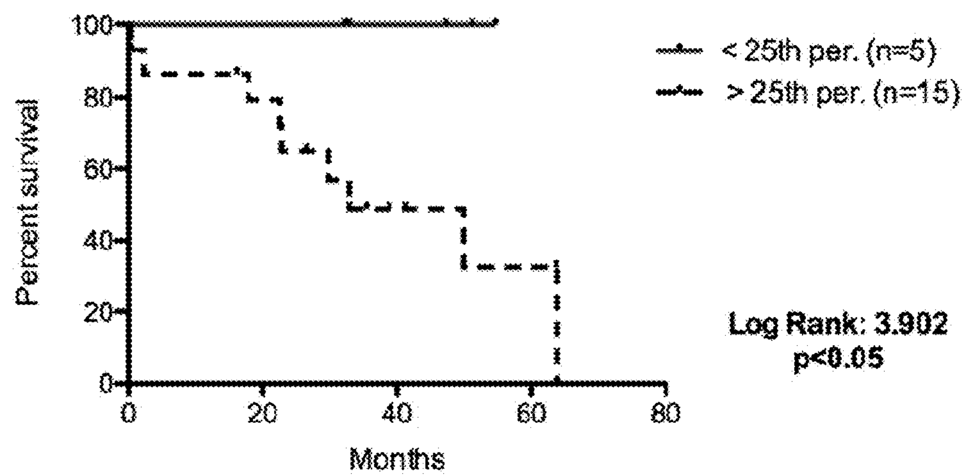
B. linc00340(v9)
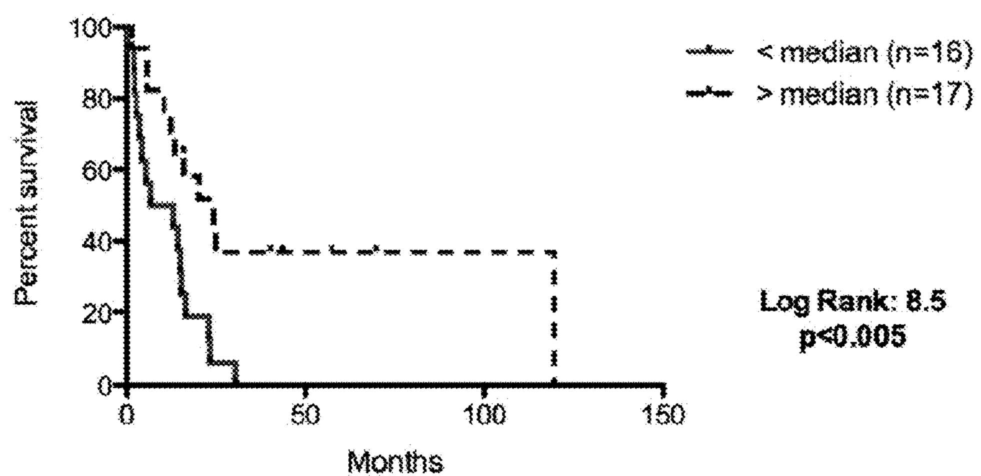

FIGURE 7
A.
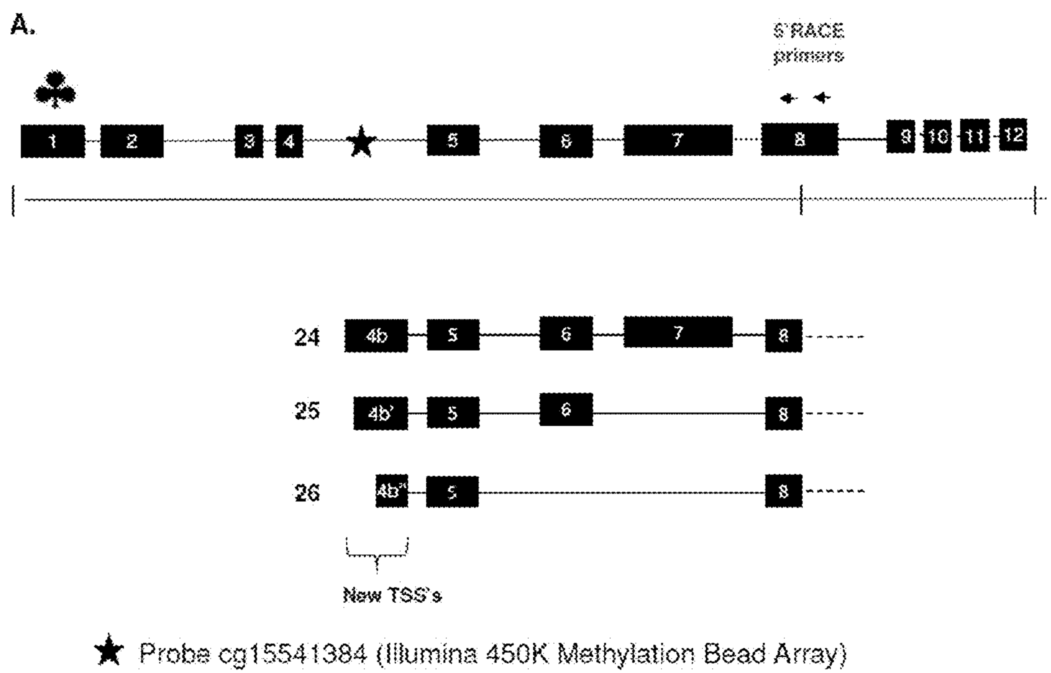
B.
linc00340(24-26)
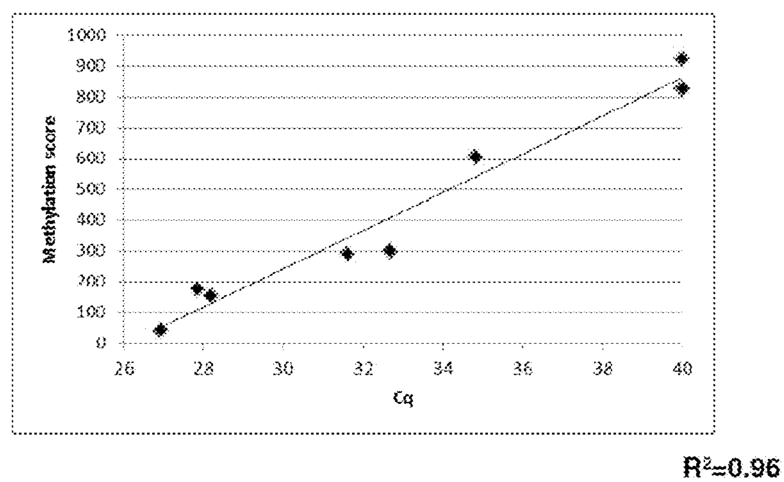
$R^2$=0.96

FIGURE 8

| Variant ID | Exons | 3'end nucleotide position* | Sequence | SEQ ID NO: |
|---|---|---|---|---|
| v1 | 8,11,12 | 22194629 | ATGAGTGAGGATCAATGGGAAGAAGAGAGCCAGCCAGTTCTGGAG<br>ACCAGAAGGCCAAAATCAAAAGTATGGGCAGGCTTGATTTCTTTAG<br>AAGACTCCAGCGGAGAACTGTGTCTCCTTGCTTCTGATTCTACATCT<br>CCATCCATGGGCCACTGTTTCAGCAACCTCAGCCAGTGCAACACAA<br>CCTCAGCCAAGAAGAGTATGCAGAGAAAGGAGTCCCCTACCTGCCA<br>CAAAACTGTTGTCTGAAAACTGTCTCATATTGCCTCAAGTTGTCATT<br>CATTGTGAATTAGACCTGTTTAACATGTAATCTGCAACATGCTTCAC<br>TGTCTAATTTTCCAGAGCCCCTCATATAAGGAACTGTATTATTGGTA<br>TAATCATCATGGTGAAGAAGTTGGTATGTGGGGGAGAGATGACAG<br>AAACAGAGAGTAAGTCAGAGCTGGCTGCCTGACAGATAAAAAGGA<br>AATGACCAAAAAAAAAAAAA | 1 |
| v2 | 8,11,12' | 22194449 | ATGAGTGAGGATCAATGGGAAGAAGAGAGCCAGCCAGTTCTGGAG<br>ACCAGAAGGCCAAAATCAAAAGTATGGGCAGGCTTGATTTCTTTAG<br>AAGACTCCAGCGGAGAACTGTGTCTCCTTGCTTCTGATTCTACATCT<br>CCATCCATGGGCCACTGTTTCAGCAACCTCAGCCAGTGCAACACAA<br>CCTCAGCCAAGAAGAGTATGCAGAGAAAGGAGTCCCCTACCTGCCA<br>CAAAACTGTTGTCTGAAAACTGTCTCATATTGTCTCAAGTTGTCATT<br>CATTGTGAATTAGACCTGTTTAACATACAAAAAAAAAAAAA | 2 |
| v3 | 8,11,12" | 22194604 | ATGAGTGAGGATCAATGGGAAGAAGAGAGCCAGCCAGTTCTGGAG<br>ACCAGAAGGCCAAAATCAAAAGTATGGGCAGGCTTGATTTCTTTAG<br>AAGACTCCAGCGGAGAACTGTGTCTCCTTGCTTCTGATTCTACATCT<br>CCATCCATGGGCCACTGTTTCAGCAACCTCAGCCAGTGCAACACAA<br>CCTCAGCCAAGAAGAGTATGCAGAGAAAGGAGTCCCCTACCTGCCA<br>CAAAACTGTTGTCTGAAAACTGTCTCATATTGTCTCAAGTTGTCATT<br>CATTGTGAATTAGACCTGTTTAACATGTAATCTGCAACATGCTTCAC<br>TGTCTAATTTTCCAGAGCCCCTCATATAAGGAACTGTATTATTGGTA<br>TAATCATCATGGTGAAGAAGTTGGTATGTGGGGGAGAGATGACAG<br>AAACAGAGAGAAAGTCGGAGCTGGCTGCCTGACAGACAAAAAAAA<br>AAAA | 3 |
| v4 | 8,9,11,12 | 22194629 | ATGAGTGAGGATCAATGGGAAGAAGAGAGCCAGCCAGGAAGTTGA<br>AGATTTGTCCAGGAGCAGATAGCCGAAGAGAGAGAGAGAGAAGAG<br>AGAACGGCTTACAGCTCAGGTCCTCTCTCCATGCTTAGGAACCACT<br>ACAAATGCTACTGCCTTGAGTCTCATTTTGTTTCCCTCTGGAAACCA<br>CATGTGTACCTTGTTTGCAACAGTATGGGTATGGAGACCAGAAGGC<br>CAAAATCAAAAGTATGGGCAGGCTTGATTTCTTTAGAAGGCTCCAG<br>CGGAGAACTGTGTCTCCTTGCTTCTGATTCTACATCTCCATCCATGG<br>GCCACTGTTTCAGCAACCTCAGCCAGTGCAACACAACCTCAGCCAA<br>GAAGAGTATGCAGAGAAAGGAGTCCCCTACCTGCCACAAAACTGTT<br>GTCTGAAAACTGTCTCATATTGTCTCAAGTTGTCATTCATTGTGAAT<br>TAGACCTGTTTAACATGTAATCTGCAACATGCTTCACTGTCTAATTT<br>TCCAGAGCCCCTCATATAAGGAACTGTATTATTGGTATAATCATCAT<br>GGTGAAGAAGTTGGTATGTGGGGGAGAGATGACAGAAACAGAGAG<br>TAAGTCAGAGCTGGCTGCCTGACAGATAAAAAGGAAATGACCAAA<br>AAAAAAAAA | 4 |
| v5 | 8,9',11,12 | 22194629 | ATGAGTGAGGATCAATGGGAAGAAGAGAGCCAGCCAGGAAGTTGA<br>AGATTTGTCCAGGAGCAGATAGCTGAAGAGAGAGAGAGAGAAGAG<br>AGAACGGCTTGCAGCTCAGTTCTGGAGACCAGAAGGCCAAAATCA<br>AAAGTATGGGCAGGCTTGATTTCTTTAGAAGACTCCAGCGGAGAAC<br>TGTGTCTCCTTGCTTCTGATTCTACATCTCCATCCATGGGCCACTGTT<br>TCAGCAACCTCAGCCAGTGCAACACAACCTCAGCCAAGAAGAGTAT<br>GCAGAGAAAGGAGTCCCCTACCTGCCACAAAACTGTTGTCTGAAAA<br>CTGTCTCATATTGTCTCAAGTTGTCATTCATTGTGAATTAGACCTGT<br>TTAACATGTAATCTGCAACATGCTTCACTGTCTAATTTTCCAGAGCC<br>CCTCATATAAGGAACTGTATTATTGGTATAATCATCATGGTGAAGA<br>AGTTGGTATGTGGGGGAGAGATGACAGAAACAGAGGGTAAGTCAG<br>AGCTGGCTGCCTGACAGATAAAAAGGAAATGACCAAAAAAAAAAAA<br>AA | 5 |

FIGURE 8 (cont'd)

| | | | | |
|---|---|---|---|---|
| v6 | 8,9,11,12''' | 22194453 | ATGAGTGAGGATCAATGGGAAGAAGAGAGCCAGCCAGGAAGTTGA<br>AGATTTGTCCAGGAGCAGATAGCTGAAGAGAGAGAGAGAGAAGAG<br>AGAACGGCTTACAGCTCAGTTCTGGAGACCAGAAGGCCAAAATCA<br>AAAGTATGGGCAGGCTTGATTTCTTTAGAAGACTCCAGCGGAGAAC<br>TGTGTCTCCTTGCTTCTGATTCTACATCTCCATCCATGGGCCACTGTT<br>TCAGCAACCTCAGCCAGTGCAACACAACCTCAGCCAAGAAGAGTAT<br>GCAGAGAAAGGAGTCCCCTACCTGCCACAAAACTGTTGTCTGAAAA<br>CTGTCTCATATTGTCTCAAGTTGTCATTCATTGTGAATTAGACCTGT<br>TTAACATGTAAAAAAAAAAAAAAA | 6 |
| v7 | 8,9',11,12'''' | 22194460 | ATGAGTGAGGATCAATGGGAAGAAGAGAGCCAGCCAGGAAGTTGA<br>AGATTTGTCCAGGAGCAGATAGCTGAAGAGAGAGAGAGAGAAGAG<br>AGAACGGCTTACAGCTCAGTTCTGGAGACCAGAAGGCCAAAATCA<br>AAAGTATGGGCAGGCTTGATTTCTTTAGAAGACTCCAGCGGAGAAC<br>TGTGTCTCCTTGCTTCTGATTCTACATCTCCATCCATGGGCCACTGTT<br>TCAGCAACCTCAGCCAGTGCAACACAACCTCAGCCAAGAAGAGTAT<br>GCAGAGAAAGGAGTCCCCTACCTGCCACAAAACTGTTGTCTGAAAA<br>CTGTCTCATATTGTCTCAAGTTGTCATTCATTGTGAATTAGACCTGT<br>TTAACATGTAATCTGCAAAAAAAAAAAAAA | 7 |
| v8 | 8,9',11,12'' | 22194604 | ATGAGTGAGGATCAATGGGAAGAAGAGAGCCAGCCAGGAAGTTGA<br>AGATTTGTCCAGGAGCAGATAGCTGAAGAGAGAGAGAGAGAAGAG<br>AGAACGGCTTACAGCTCAGTTCTGGAGACCAGAAGGCCAAAATCA<br>AAAGTATGGGCAGGCTTGATTTCTTTAGAAGACTCCAGCGGAGAAC<br>TGTGTCTCCTTGCTTCTGATTCTACATCTCCATCCATGGGCCACTGTT<br>TCAGCAACCTCAGCCAGTGCAACACAACCTCAGCCAAGAAGAGTAT<br>GCAGAGAAAGGAGTCCCCTACCTGCCACAAAACTGTTGTCTGAAAA<br>CTGTCTCATATTGTCTCAAGTTGTCATTCATTGTGAATTAGACCTGT<br>TTAACATGTAATCTGCAACATGCTTCACTGTCTAATTTTCCAGAGCC<br>CCTCATATAAGGAACTGTATTATTGGTATAATCATCATGGTGAAGA<br>AGTTGGTATGTGGGGGAGAGATGACAGAAACAGAGAGAAAGTCAG<br>AGCTGGCTGCCTGACAGACAAAAAAAAAAAA | 8 |
| v9 | 8,10,11,12''' ' | 22194460 | ATGAGTGAGGATCAATGGGAAGAAGAGAGCCAGCCAGGCTCACAG<br>GCAGAAGGAATTTTCCTTGTCTTGGATGAGACTTTTGACTTGGACTT<br>TTGGGTTAAGTTCTGGAGACCAGAAGGCCAAAATCAAAAGTATGGG<br>CAGGCTTGATTTCTTTAGAAGACTCCAGCGGAGAACTGTGTCTCCTT<br>GCTTCTGATTCTACATCTCCATCCATGGGCCACTGTTTCAGCAACCT<br>CAGCCAGTGCAACACAACCTCAGCCAAGAAGAGTATGCAGAGAAA<br>GGAGTCCCCTACCTGCCACAAAACTGTTGTCTGAAAACTGTCTCAT<br>ATTGTCTCAAGTTGTCATTCATTGTGAATTAGACCTGTTTAACATGT<br>AATCTGCAAAAAAAAAAAAA | 9 |
| v10 | 8,9,13 | 22214735 | ATGAGTGAGGATCAATGGGAAGAAGAGAGCCAGCCAGGAAGTTGA<br>AGATTTGTCCAGGAGCAGATAGCTGAAGAGAGAGAGAGAGAAGAG<br>AGAACGGCTTACAGCTCAGGTCCTCTCCCCATGCTTAGGAACCACT<br>ACAAATGCTACTGCCTTGAGTCTCATTTTGTTTCCCTCTGGAAACCA<br>CATGTGTACCTTGTTTGCAACAGTATGGGGCACCGAGGAAGAGAAC<br>CAATGGCAGAGGCCACATGTGCAAGCAAGATGGGAGTCTGGAGAG<br>CCTCAGGCTAAATCACGAGTGCTCAGCCCTCTCCTCTTTGTAAGGGC<br>AACCGGGTCATATCTGCCAGCATAGAACTGCTCTGTCCACAGCCCT<br>AAAATCTAATACCTAGAACAATAAATGCACTTAAGCACGTCAAAAA<br>AAAAAAAA | 10 |
| v11 | 8,9',13 | 22214735 | ATGAGTGAGGATCAATGGGAAGAAGAGAGCCAGCCAGGAAGTTGA<br>AGATTTGTCCAGGAGCAGATAGCTGAAGAGAGAGAGAGAGAAGAG<br>AGAACGGCTTACAGCTCAGGGCACCGAGGAAGAGAACCAATGGCA<br>GAGGCCACATGTGCAAGCAAGATGGGAGTCTGGAGAGCCTCAGGC<br>TAAATCACGAGTGCTCAGCCCTCTCCTCTTTGTAAGGGCAACCGGG<br>TCATATCTGCCAGCATAGAACTGCTCTGTCCACAGCCCTAAAATCTA<br>ATACCTAGAACAATAAATGCACTTAAGCACGTAAAAAAAAAAAAA | 11 |

FIGURE 8 (cont'd)

| | | | | |
|---|---|---|---|---|
| v12 | 8,10,13 | 22214735 | ATGAGTGAGGATCAATGGGAAGAAGAGAGCCAGCCAGGCTCACAGGCAGAAGGAATTTTCCTTGTCTTGGATGAGACTTTTGACTTGGACTTTTGGGTTAAGGGCACCGAGGAAGAGAACCAATGGCAGAGGCCACATGTGCAAGCAAGATGGGAGTCTGGAGAGCCTCAGGCTAAATCACGAGTGCTCAGCCCTCTCCTCTTTGTAAGGGCAACCGGGTCATATCTGCCAGCATAGAACTGCTCTGTCCACAGCCCTAAAATCTAATACCTAGAACAATAAATGCACTTAAGCACGTCAAAAAAAAAAAA | 12 |
| v13 | 8,13 | 22214735 | ATGAGTGAGGATCAATGGGAAGAAGAGAGCCAGCCAGGGCACCGAGGAAGAGAACCAATGGCAGAGGCCACATGTGCAAGCAAGATGGGAGTCTGGAGAGCCTCAGGCTAAATCACGAGTGCTCAGCCCTCTCCTCTTTGTAAGGGCAACCGGGTCATATCTGCCAGCATAGAACTGCTCTGTCCACAGCCCTAAAATCTAATACCTAGAACAATAAATGCACTTAAGCACGTCAAAAAAAAAAAAA | 13 |
| v14 | 8,9" | 22111020 | ATGAGTGAGGATCAATGGGAAGAAGAGAGCCAGCCAGGAAGTTGAAGATTTGTCCAGGAGCAGATAGCTGAAGAGGGAGAGAAAAAAAAAAAA | 14 |
| v15 | 8,9'" | 22111164 | ATGAGTGAGGATCAATGGGAAGAAGAGAGCCAGCCAGGAAGTTGAAGATTTGTCCAGGAGCAGATAGCTGAAGAGAGAGAGAGAGAAGAGAGAACGGCTTACAGCTCAGGTCCTCTCTCCATGCTTAGGAACCACTACAAATGCTACTGCCTTGAGTCTCATTTTGTTTCCCTCTGGAAACCACATGTGTACCTTGTTTGCAACAGTATGGGTATGGATGTTTTGGCAAAAAAAAAAAAA | 15 |
| v16 | 8,9"" | 22111240 | ATGAGTGAGGATCAATGGGAAGAAGAGAGCCAGCCAGGAAGTTGAAGATTTGTCCAGGAGCAGATAGCTGAAGAGAGAGAGAGAGAAGAGAGAACGGCTTACAGCTCAGGTCCTCTCTCCATGCTTAGGAACCACTACAAATGCTACTGCCTTGAGTCTCATTTTGTTTCCCTCTGGAAACCACATGTGTACCTTGTTTGCAACAGTATGGGTATGGATGTTTTGGTAGTTCTTACACATTTATTTTAAAATTTAAAGAAGTAGTGCCATAAAGCTTTATCAGGATGTATTTAAAATGAAAAAAAAAAAAA | 16 |
| v17 | 8,9""' | 22111375 | ATGAGTGAGGATCAATGGGAAGAAGAGAGCCAGCCAGGAAGTTGAAGATTTGTCCAGGAGCAGATAGCTGAAGAGAGAGAGAGAGAAGAGAGAACGGCTTACAGCTCAGGTCCTCTCTCCATGCTTAGGAACCACTACAAATGCTGCTGCCTTGAGTCTCATTTTGTTTCCCTCTGGAAACCACATGTGTACCTTGTTTGCAACAGTATGGGTATGGATGTTTTGGTAGTTCTTACACATTTATTTTAAAATTTAAAGAAGTAGTGCCATAAAGCTTTATCAGGATGTATTTAAAATGAAAATAGTCTCTTGTTATCTAGCATGCAACTGATTCTTTCAATTTGGTTTGGTTAGTCAGAATCTTACCAGAAGTCTGTCCAGGTGATAGGTTAGTTGAGAGCATCAAGACCAACCAAAATAAAACAAAAACAATAGCCGAAAAAAAAAAAAA | 17 |
| v18 | 8,8b | 22083860 | ATGAGTGAGGATCAATGGGAAGAAGAGAGCCAGCCAGCTCTGTATTCTAAGAACCTGGAAACAATCTTTATTCACACCGTTAAGACCAAAAAAAAAAAAA | 18 |
| v19 | 8 | 22056914 | ATGAGTGAGGATCAATGGGAAGAAGAGAGCCAAAAAAAAAAAA | 19 |

*Homo sapiens chromosome 6, GRCh37.p10 Primary Assembly

FIGURE 9

| Variant ID | Exons | 3'end nucleotide position* | Sequence | SEQ ID NO: |
|---|---|---|---|---|
| v20 | 11,12'''' | 22194464 | CTGTGTCTCCTTGCTTCTGATTCTACATCTCCATCCATGGGCCACTGTTTCAGCAACCTCAGCCAGTGCAACACAACCTCAGCCAAGAAGAGTATGCAGAGAAAGGAGTCCCCTACCTGCCACAAAACTGTTGTCTGAAAACTGTCTCATATTGTCTCAAGTTGTCATTCATTGTGAATTAGACCTGTTTAACATGTAATCTGCAACATGAAAAAAAAAAAAAA | 20 |
| v21 | 11,12''''' | 22194450 | CTGTGTCTCCTTGCTTCTGATTCTACATCTCCATCCATGGGCCACTGTTTCAGCAACCTCAGCCAGTGCAACACAACCTCAGCCAAGAAGAGTATGCAGAGAAAGGAGTCCCCTACCTGCCACAAAACTGTTGTCTGAAAACTGTCTCATATTGTCTCAAGTTGTCATTCATTGTGAATTAGACCTGTTTAACATGGAAAAAAAAAAAAAA | 21 |
| v22 | 11,12'''''' | 22194403 | CTGTGTCTCCTTGCTTCTGATTCTACATCTCCATCCATGGGCCACTGTTTCAGCAACCTCAGCCAGTGCAACACAACCTCAGCCAAGAAGAGTATGCAGAGAAAGGAGTCCCCTACCTGCCACAAAACTGTTGTCTGAAAACTGTCTCAAAAAAAAAAAAAA | 22 |
| v23 | 11,12''''''' | 22194400 | CTGTGTCTCCTTGCTTCTGATTCTACATCTCCATCCATGGGCCACTGTTTCAGCAACCTCAGCCAGTGCAACACAACCTCAGCCAAGAAGAGTATGCAGAGAAAGGAGTCCCCTACCTGCCACAAAACTGTTGTCTGAAAACTGTCAAAAAAAAAAAAAA | 23 |

*Homo sapiens chromosome 6, GRCh37.p10 Primary Assembly

FIGURE 10

| Variant ID | Exons | 5'end nucleotide position* | Sequence | SEQ ID NO: |
|---|---|---|---|---|
| v24 | 4b,5,6,7,8 | 21886326 | TATAGAAAGCAGCACACATGACCTCTGTCCTTCCAGCTGCCACCAG<br>TTTCTGGGTTGTCGAGTGATACCCTGAAAGTTTACAGTCAACACTCC<br>TTGTGTGGGGTCAGTCCTAGAAATGGCGACGCTGCTCTCCGAAGAT<br>AGGAAAGAAGAGGACCTCATTCCATTGAGCCATTGACCGAAATATT<br>TTCTCAACAAAGTTGAACTGAGCTGAAACTGTGTGAATCATGGCAA<br>TACAGTGAAAGACAGTGATTTACTGCTTTTGAGGGCGTGCATGTAT<br>ATGATTAACGGATGGAAGTGCAGGACTCCAAGATTTACTTCCTTCC<br>CTTTCCAGCAGAATTACCTGAGACGAGTAAAATCTACTGGTGGAGT<br>CACTCCATTATTCTTATCTGTGGAGATCTAGATCTTGATTTGAAAGT<br>TTCTGAGAAAATCTTCAGCTCAGACTTGAGGGTCAACTTTACCAGCT<br>GAAGGATCTGCATTTACTGCTCAACCACATCTAATTTGATGTCCTCT<br>GCAGATTTAAAATGTGTGCCTTCTTTTCCGTCACCAAGTCATCCCTG<br>GGTTACTACTGAACATCCTTCTCAATTCCCCCCGACCCATGGATGGC<br>TGTTCTCCATTGTCTGTTTCACCAGATGTCCTCAAAACAAACAGACA<br>GAAGAAGGAAGTGGCTAATGGAGCTGTGGAGTCCAAGTGTGACTG<br>CCAAGAGGAATCCAGCAAAGC | 24 |
| v25 | 4b',5,6,8 | 21886339 | ACACATGACCTCTGTCCTTCCAGCTGCCACCAGTTTCTGGGTTGTCG<br>AGTGATACCCTGAAAGTTTACAGTCAACACTCCTTGTGTGGGGTCA<br>GTCCTAGAAATGGCGACGCTGCTCTCCGAAGATAGGAAAGAAAAG<br>GACCTCATTCCATTGAGCCATTGACCGAAATATTTTCTCAACAAAGT<br>TGAACTGAGCTGAAACTGTGTGAATCATGGCAATACAGTGAAAGAC<br>AGTGATTTACTGCTTTTGAGGGCGTGCATGTATATGATTAACGGATG<br>GAAGTGCAGGACTCCAAGATTTACTTCCTTCCCTTTCCAGCAGAATT<br>ACCTGAGACGAGTAAAATCTACTGGTGGAGTCACTCCATTATTCTT<br>ATCTGTGGAGATCTAGATCTTGATTTGAAAGTTTCTGAGAAAATCTT<br>CAGCTCAGACTTGAGGGTCAACTTTACCAGCTGAAGGAGCTGTGGA<br>GTCCAAGTGTGACTGCCAAGAGGAATCCAGCAAAGC | 25 |
| v26 | 4b'',5,8 | 21886431 | AGTCCTAGAAATGGCGACGNTGCTCTCCGAAGATAGGAAAGAAAA<br>GGACCTCATTCCATTGAGCCATTGACCGAAATATTTTCTCAACAAA<br>GTTGAACTGAGCTGAAACTGTGTGAATCATGGCAATACAGTGAAAG<br>ACAGTGATTTACTGCTTTTGAGGGCGTGCATGTATATGATTAACGG<br>ATGGAAGTGCAGGACTCCAAGATTTACTTCCTTCCCTTTCCAGCAGA<br>ATTACCTGAGACGAGAGCTGTGGAGTCCAAGTGTGACTGCCAAGAG<br>GAATCCAGCAAAGC | 26 |

*Homo sapiens chromosome 6, GRCh37.p10 Primary Assembly

FIGURE 11

```
   1 gtctgctccg ggacttggaa caaaaggggg aactctgatg aactctcttt cctcccctct
  61 cccccggacg ccggggtatc tccctctcgc aactttgccg ccccgacttt ctctgctgtc
 121 aggccgggaa aaagtgtccg aacgcctcgt ggactgcagc gggggaaatg tcccttaaaa
 181 gtgcgacgaa gtggggaaga aggtgtaatt actattatca gcatctagaa agcatcatga
 241 atttgctgga gtacttccta gcactgacct ccttcattct gcgttgttct tactggatct
 301 ttccatcagc caacaatatg gaagtaccaa tacaaggtca aatcattcct ggattcatct
 361 ggagttgctt aaaagttaaa tcattggaat ttttgatgat acctttttcta tatggattac
 421 aatttgatcg ctgggaattc tccaccttaa agaagtaccc tcaggtgact acagatgtgt
 481 taacacccag catgttccgg taggagactt tctggatggg gaagatttcc aggaattggc
 541 aacaagctca tttcactggt gggtttgctg aagcattatc acaagacagt cagaatgact
 601 gatgagtgct cttcaggtgt gaatcatggc aatacagtga aagacagtga tttactgctt
 661 ttgagggcgt gcatgtatat gattaacgga tggaagtgca ggactccaag atttacttcc
 721 ttccctttcc agcagaatta cctgagacga gtaaaatcta ctggtggagt cactccatta
 781 ttcttatctg tggagatcta gatcttgatt tgaaagtttc tgagaaaatc ttcagctcag
 841 acttgagggt caactttacc agctgaagga tctgcattta ctgctcaacc acatctaatt
 901 tgatgtcctc tgcagattta aaatgtgtgc cttctcttcc gtcaccaagt catccctggg
 961 ttactactga acatccttct caattccccc cgacccatgg atggctgttc tccattgtct
1021 gtttcaccag atgtcctcaa aacaaacaga cagaagaagg aagtggctaa tggagctgtg
1081 gagtccaagt gtgactgcca agaggaatcc agcaaagcca aaaagcccaa gcatgtagcc
1141 ctgcccgaag cacgccacac gcatggaaaa cccagaggaa atgagtgagg atcaatggga
1201 agaagagagc cagccaggaa gttgaagatt tgtccaggag cagatagctg aagagagaga
1261 gagagaagag agaacggctt acagctcagg tcctctctcc atgcttagga accactacaa
1321 atgctactgc cttgagtctc attttgtttc cctctggaaa ccacatgtgt accttgtttg
1381 caacagtatg ggctcacagg cagaaggaat tttccttgtc ttggatgaga cttttgactt
1441 ggacttttgg gttaagttct ggagaccaga aggccaaaat caaaagtatg ggcaggcttg
1501 atttctttag aagactccag cggagaactg tgtctccttg cttctgattc tacatctcca
1561 tccatgggcc actgtttcag caacctcagc cagtgcaaca caacctcagc caagaagagt
1621 atgcagagaa aggagtcccc tacctgccac aaaactgttg tctgaaaact gtctcatatt
1681 gtctcaagtt gtcattcatt gtgaattaga cctgtttaac atgtaatctg caacatgctt
1741 cactgtctaa ttttccagag cccctcatat aaggaactgt attattggta taatcatcat
1801 ggtgaagaag ttggtatgtg ggggagagat gacagaaaca gagagtaagt cagagctggc
1861 tgcctgacag ataaaaagga aatgaccaaa aaaaaaaaaa aaaa
```

LONG NONCODING RNA (LNCRNA) AS A BIOMARKER AND THERAPEUTIC MARKER IN CANCER

CROSS-REFERENCE TO RELATED APPLICATIONS

This application claims benefit to U.S. Provisional Patent Application No. 61/565,424, filed Nov. 30, 2011, which is incorporated herein by reference.

BACKGROUND

Long noncoding RNAs (lncRNAs) are defined as RNA molecules greater than 200 nucleotides in length that have low protein-coding potential. Traditionally viewed as transcriptional noise, they are now emerging as important regulators of cellular functions such as protein synthesis, RNA maturation/transport, chromatin remodeling, and transcriptional activation and/or repression programs. They have been shown to influence biological processes such as stem cell pluripotency, cell cycle, and DNA damage response. Indicative of their important regulatory functions, aberrant expression and function of some lncRNAs have been observed in several types of cancers.

New diagnostic and prognostic biomarkers are needed for early recognition and effective management of cancer. Given the important regulatory role of lncRNAs, it would be desirable to identify aberrantly expressed lncRNAs that may be used as cancer biomarkers and targets for molecular therapeutics.

SUMMARY

In some embodiments, novel lnc00340 variants are provided. Such variants may be any variants detected in the locus, including, but not limited to, those including a nucleotide sequence selected from SEQ ID NO:1-26.

In some embodiments, methods of diagnosing a cancer (e.g., cutaneous melanoma) in a subject are provided. Such methods may include steps of isolating one or more lncRNA transcripts (e.g., one or more lnc00340 variants) in a biological sample from the subject; measuring a test level of the one or more isolated lncRNA transcripts; comparing the test level to a control level (eg.: non-cancer level) of the one or more lncRNA transcripts; and diagnosing a subject as having the cancer when the test level is higher than the control level.

In other embodiments, methods of determining the progression of a cancer (e.g., cutaneous melanoma) in a subject are provided. Such methods may include steps of measuring a test level of one or more lncRNA transcripts in a biological sample from the subject; comparing the test level to a control level of the one or more lncRNA transcripts; and differentiating between an early stage cancer (e.g., primary tumor) and a later stage (metastatic cancer) or more aggressive tumor when the lncRNA test level is higher than the control level (eg.: non-cancer level).

In other embodiments, methods of determining a prognosis of a subject having a cancer (e.g., cutaneous melanoma) are provided. Such methods may include steps of isolating one or more lncRNA transcripts in a biological sample from the subject; measuring a test level of the one or more isolated lncRNA transcripts assigning the test level to a high expression level or a low expression level relative to a cutoff value (e.g., a baseline, cutoff or threshold) level; and determining a prognosis for the subject having the cancer based on the test level relative to the cutoff value level. The prognosis may be, for example, a poor prognosis or a good prognosis, measured by a shortened survival or a prolonged survival, respectively. Further, the survival may be measured as an overall survival (OS), disease-free survival (DFS), or recurrence-free survival (RFS).

In one embodiment, the cancer is primary melanoma cancer; and the prognosis for a high expression level is poor and the prognosis for a low expression level is good. In this case, the method may additionally include administering a therapeutically effective dose of one or more therapeutic agents to the subject when the test level is a high expression level. In another embodiment, the cancer is metastatic melanoma cancer; and the prognosis for a high expression level is good relative to a low expression level. In this case, the method may additionally include administering a therapeutically effective dose of one or more therapeutic agents to the subject.

In additional embodiments, a method of treating a cancer (e.g., cutaneous melanoma) in a subject is provided. The method may include administering, to the subject, an effective amount of a therapeutic agent, such as an inhibiting or activating agent that inhibits or activates one or more physiological actions of the lncRNA transcript, respectively.

In the embodiments provided above, the one or more lncRNA transcripts may be transcribed from the 6p22.3 genomic locus, between nucleotide 21598851 to nucleotide 22287474. In one embodiment, the lncRNA transcript is a linc00340 transcript.

BRIEF DESCRIPTION OF THE DRAWINGS

FIG. 1A shows relative levels of linc00340 between normal melanocytes and melanoma cell lines; and FIG. 1B shows relative levels of linc00340 between normal melanocytes, AJCC Stage III, and AJCC Stage IV melanoma cell lines. Error bars indicate the standard error of the mean. Levels of linc00340 were normalized to SDHA housekeeping transcript levels using the delta-delta Cq method.

FIG. 2A shows variants linc00340v1 to linc00340v19 (SEQ ID NO:1 to SEQ ID NO:19, respectively) that were cloned using 3'-rapid amplification of cDNA ends (3' RACE) using primers targeting exon 8 of the parent linc00340 transcript (top ♣).

FIG. 4 illustrates that tissue expression of linc00340 RNA correlates with melanoma progression. FIG. 4A shows that linc00340(v1-19) expression increases progessively from non-cancer tissues to primary and metastatic melanoma ($p=0.05$, One-way ANOVA). The levels are linc00340(v1-19) are significantly increased in both primary and metastatic melanoma compared to non-cancer tissues (**$p<0.01$ and *$p<0.05$, respectively, t-test). FIG. 4B shows that linc00340 (v9) expression increases progressively from non-cancer tissues to primary and metastatic melanoma (p=0.02, One-Way ANOVA). The levels are linc00340(v9) are significantly increased in both primary and metastatic melanoma compared to non-cancer tissues (**p<0.01, t-test). Horizontal bars indicate the median. Levels of linc00340 variants were normalized to SDHA housekeeping transcript levels using the delta-delta Cq method.

FIG. 6 illustrates the prognostic value of RNA transcripts expressed from the linc00340 locus. FIG. 6A is a Kaplan-Meier curve showing that high levels of linc00340(v1-19) in primary melanoma tumors are associated with shorter survival (Log Rank 3.9, p<0.05). FIG. 6B is a Kaplan-Meier curve showing that low levels of linc00340(v9) in metastatic melanoma tumors are associated with shorter survival (Log Rank 8.5, p<0.005).

FIG. 7A is a representation of novel linc00340 transcriptional start sites (TSS) and additional splice variants identified by 5'-rapid amplification of cDNA ends (5'RACE) in melanoma cells.

FIG. 7B shows that CpG site DNA methylation within the new TSS is inversely correlated with linc00340 expression, indicating that DNA methylation can be a surrogate for linc00340 expression.

FIG. 8 is a table showing the nucleotide sequence of linc00340 variants v1 to v19 (linc00340v1-linc00340v19; SEQ ID NO:1 to SEQ ID NO:19, respectively) identified by 3'-rapid amplification of cDNA ends (3' RACE) using primers targeting exon 8 of the parent linc00340 transcript (SEQ ID NO:27).

FIG. 9 is a table showing the nucleotide sequence of linc00340 variants v20 to v23 (linc00340v20 to linc00340v23; SEQ ID NO:20 to SEQ ID NO:23, respectively) identified by 3'-rapid amplification of cDNA ends (3' RACE) using primers targeting exons 10-11 of the parent linc00340 transcript (SEQ ID NO:27).

FIG. 10 is a table showing the nucleotide sequence of linc00340 variants v24 to v26 (linc00340v24 to linc00340v26; SEQ ID NO:24 to SEQ ID NO:26, respectively) identified by 5'-rapid amplification of cDNA ends (5' RACE) using primers targeting exon 8 of the parent linc00340 transcript (SEQ ID NO:27).

FIG. 11 shows the sequence of the parent linc00340 transcript (SEQ ID NO:27) (Gene ID: 401237; RefSeq ID: NR_015410.1).

DETAILED DESCRIPTION

Figure 1A:
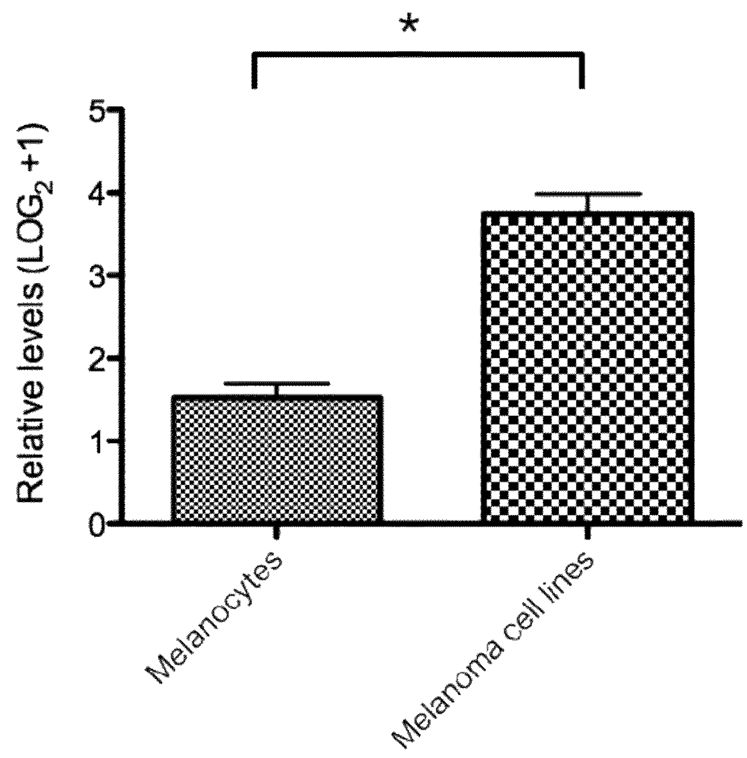
FIGS. 1A and 1B illustrates that the linc00340 locus is overexpressed in melanoma cell lines. (*$p<0.05$; Mann-Whitney test or t-test).

Long noncoding RNAs (lncRNAs) that may be used as cancer biomarkers and methods of diagnosing, prognosing and monitoring cancer including, but not limited to, cutaneous melanoma using said lncRNAs are provided herein. Cutaneous melanoma is the most lethal form of skin cancer and has the fastest rising incidence among all cancers in the United States. Diagnostic and prognostic biomarkers are needed for early recognition and effective management metastatic melanoma.

Because lncRNAs have emerged as important regulators of gene expression and cell behavior, and have been shown to repress or promote tumor growth and metastasis, lncRNAs may be used as a cancer biomarker in melanoma and other cancers discussed below. Such lncRNAs may be transcribed from any genomic region, including, but not limited to, intergenic lncRNA or intervening non-coding RNA (lincRNA), which refers to lncRNA transcripts that are located between two protein-coding genes and transcribed from the + and/or −DNA strand(s); and intragenic lncRNA, which refers to lncRNA transcripts that are located within a protein-coding gene. Intragenic lncRNA may be located within a coding region (i.e., an exon) of the gene and/or within a non-coding region (i.e., an intron) of the protein-coding gene, and transcribed from the + and/or −DNA strand(s).

As described further below, a screen for non-coding genomic regions that are altered in metastatic melanoma was performed, and a large intergenic non-coding RNA (lincRNA) locus on chromosome 6p was identified as frequently amplified in circulating tumor cells (CTCs) and metastatic tumors. The lncRNA locus identified is part of the 6p22.3 genomic locus, which is amplified in metastatic melanoma and melanoma circulating tumor cells. The intergenic 6p22.3 region, which is between the SOX4 and PRL genes (nucleotide 21598851 to nucleotide 22287474), is transcribed into several long non-coding RNAs (lncRNAs) of different sizes. One such lncRNA is a linc00340 transcript (FIG. 11; SEQ ID NO:27; "the parent linc00340 transcript") (Gene ID: 401237; RefSeq ID: NR_015410.1). Another such lncRNA is a LOC729177 transcript (Gene ID: 729177; RefSeq ID: NR_034143.1).

Expression analysis of the several linc00340 transcripts from this locus showed higher levels in melanoma cell lines as compared to melanocytes. Additionally, it was observed that stage III cell lines derived from patients having a poor prognosis showed a tendency toward having higher levels of this transcript as compared to those from patients having a good prognosis or a better prognosis than said patients having a poor prognosis. The levels of the lncRNA transcript also showed a progressive increase from nevi to stage IV disease, and were significantly elevated in a subset of brain metastatic tumors.

In addition to the parent linc00340 transcript described above (FIG. 11, SEQ ID NO:27), several novel linc00340 transcript variants have been discovered in melanoma cell lines, as described herein. In some embodiments, the linc00340 transcript variants include one or more individual linc00340 transcript variant including, but not limited to, linc00340v1 (SEQ ID NO:1), linc00340v2 (SEQ ID NO:2), linc00340v3 (SEQ ID NO:3), linc00340v4 (SEQ ID NO:4), linc00340v5 (SEQ ID NO:5), linc00340v6 (SEQ ID NO:6), linc00340v7 (SEQ ID NO:7), linc00340v8 (SEQ ID NO:8), linc00340v9 (SEQ ID NO:9), linc00340v10 (SEQ ID NO:10), linc00340v11 (SEQ ID NO:11), linc00340v12 (SEQ ID NO:12), linc00340v13 (SEQ ID NO:13), linc00340v14 (SEQ ID NO:14), linc00340v15 (SEQ ID NO:15), linc00340v16 (SEQ ID NO:16), linc00340v17 (SEQ ID NO:17), linc00340v18 (SEQ ID NO:18), linc00340v (SEQ ID NO:19), linc00340v (SEQ ID NO:20), linc00340v21 (SEQ ID NO:21), linc00340v22 (SEQ ID NO:22), linc00340v23 (SEQ ID NO:23), linc00340v24 (SEQ ID NO:24), linc00340v25 (SEQ ID NO:25), linc00340v26 (SEQ ID NO:26), or a combination thereof (FIGS. 8-10). One skilled in the art would understand that many additional linc00340 transcript variants may also exist. Further, the linc00340 transcript variants described include the nucleic acid sequences above (SEQ ID NOs:1-26), and any variants that have at least 95%, at least 96%, at least 97%, at least 98%, at least 99% homology of SEQ ID NOs:1-26. The linc00340 transcript variants that may be used in accordance with the methods described herein are not limited to those described above. In certain embodiments, the linc00340 transcript variants may include any additional variants of the linc00340 parent transcript, as one skilled in the art would understand that many additional linc00340 transcript variants may exist and that may have differential expression found in melanoma or other cancer cells as compared to normal cells.

In some embodiments, one or more of the individual linc00340 transcript variants described above (e.g., linc00340v9) may be isolated from a biological sample (e.g., blood, serum, or tumor tissue) and measured to determine a diagnosis or prognosis or melanoma or other applicable cancer. In other embodiments a set or panel of the linc00340 transcript variants including, but not limited to, linc00340v1 to linc00340v19 ("linc00340v1-19"), linc00340v20 to linc00340v23 ("linc00340v20-23"), and linc00340v24 to linc00340v26 ("linc00340v24-26") described above may be isolated from a biological sample (e.g., blood, serum, or tumor tissue) and measured to determine a diagnosis or prognosis or melanoma or other applicable cancer.

The levels of linc00340 transcript variants showed a progressive increase from non-cancer to primary and metastatic melanoma. Human xenograft brain metastasis melanoma cell line variants obtained after 1, 2, and 3 cycles of in vivo passages in nude mice were also assessed and compared. A gradual increase in the lincRNA levels was observed after each cycle with the more aggressive variant (post cycle 3) expressing the highest levels. The more aggressive variant also displayed enriched nuclear localization compared to the parental cells (cycle 0). Moreover, the expression of linc00340 variants in primary and metastatic melanoma specimens was associated with patient survival, as described further in the Examples below. Therefore, according to certain embodiments, the linc00340 transcript and related novel variants, as well as other lncRNAs that are transcribed from the above-identified genomic locus are associated with the presence or absence of primary melanoma (e.g., AJCC Stage I or II), metastatic melanoma (e.g., AJCC Stage III or IV, including local or distant metastases or circulating tumor cells) and the progression or aggressiveness of the melanoma. The levels of lncRNA transcripts are also associated with patient survival in both primary and metastatic melanoma. Hence, linc00340 transcripts and related variants may be used as biomarkers for diagnosing, prognosing and monitoring cutaneous melanoma. Further, such diagnoses, prognoses of cutaneous melanoma based on levels of linc00430 transcripts may be used to make clinical decisions regarding optimization of a melanoma patient's treatment regimen.

Figure 12:
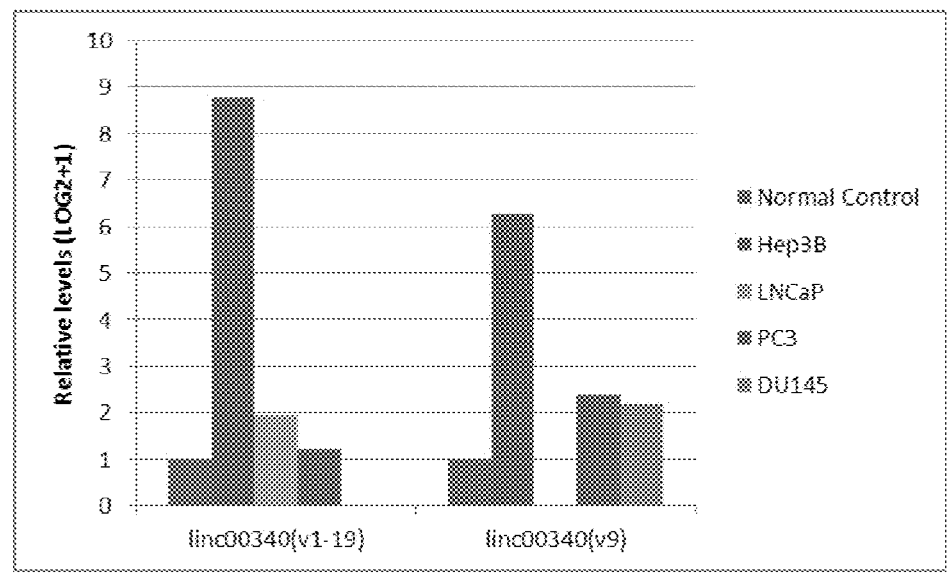
FIG. 12 is a bar graph illustrating that the linc00340 variants linc00340v1-19, and linc00340v9 are present in higher amounts in hepatocellular carcinoma and prostate cancer cell lines (Hep3B, LNCaP, PC3, and DU145) than is found in normal cells.

In other embodiments, additional lncRNA transcripts that are amplified or otherwise altered in a cancer may be identified as described above. For example, the linc00340 variants described herein have been shown to be associated with cancer cells in other cancers such as prostate and liver cancer (FIG. 12). These additional lncRNA transcripts may be used in accordance with the methods described below to diagnose, prognose, and monitor any cancer that is associated with an lncRNA transcript. Examples of cancers that may be associated with lncRNA (e.g., altered expression of lncRNA or other aberration as compared to a control) include, but are not limited to, bone cancer, bladder cancer, brain cancer, breast cancer, cancer of the urinary tract, carcinoma, cervical cancer, colon cancer, esophageal cancer, gastric cancer, head and neck cancer, hepatocellular cancer, same as HCC, lung cancer, lymphoma and leukemia, melanoma, neuroblastoma, primary brain cancer(glioma, meningiomas, glioblasatoma), ovarian cancer, pancreatic cancer, pituitary cancer, prostate cancer, rectal cancer, renal cancer, sarcoma, thyroid cancer, and uterine cancer.

Because certain lncRNA transcripts, such as the linc00340 transcripts and the linc00340v1-19 variant transcripts, have been found to be overexpressed in cancer, such transcripts may also be used as a therapeutic target in cutaneous melanoma or in other cancers discussed below that are associated with an lncRNA transcript. Therefore, according to some embodiments, an lncRNA transcript including, but not limited to the linc00340 transcript and any one or more of linc00340v1-19 variant transcripts, may be targeted using an inhibiting agent or therapeutic targeting strategy such as antisense RNA, RNA interference (RNAi), siRNA, esiRNA, shRNA, miRNA, decoys, RNA aptamers, small molecule inhibitors, RNA/DNA-binding proteins/peptides or other compounds with different formulations to inhibit one or more physiological actions effected by lncRNA.

In other embodiments, low or underexpression of some lncRNA variant transcripts (e.g., linc00340 (v7)) has been shown to be associated with a shorter survival (FIG. 6B). As such, according to some embodiments, an lncRNA transcript including, but not limited to the linc00340v7 transcript variant may be targeted using an activating agent or therapeutic targeting strategy such RNA, cDNA, RNA/DNA-binding proteins/peptides, and RNA/DNA demethylating agents promoting linc00340 expression and/or stability and/or activity.

In one embodiment such therapeutic targeting strategies may be used to develop a therapeutic or pharmaceutical agent that targets linc00340 for treating cutaneous melanoma. Treatment of cutaneous melanoma or any other cancer associated with an lncRNA transcript may include administering to a subject having the cancer an effective amount of an inhibiting agent, a therapeutic agent or a pharmaceutical agent, such as those described above.

In certain embodiments, a diagnosis or prognosis based on the methods described above may be used to optimize or select a treatment regimen for a subject. For example, a method for diagnosing or prognosing melanoma or other cancer may be performed as described above. In one embodiment, a subject that is diagnosed with primary melanoma based on expression level of linc00340 or a related variant may be treated according to FDA approved protocols standards known in the art for a particular therapeutic agent for a particular primary cancer. In the case where the cancer is melanoma, a subject that is diagnosed with a primary melanoma/regional lymph node metastatic melanoma may be administered one or more therapeutic agents including, but limited to, imiquimod, interferon, or other vaccines or treatments according to protocols and effective doses that are standard treatment in the field. Alternatively, a diagnosis of primary cancer may be treated using a "wait and see approach" after surgical resection, since such a diagnosis indicates that metastasis of the primary cancer has not occurred.

In another embodiment, a diagnosis of a subject that is diagnosed with metastatic melanoma based on an expression level of linc00340 or a related variant may be treated more aggressively according to FDA approved protocols standards known in the art for a particular therapeutic agent for a particular metastatic cancer. In the case where the cancer is melanoma, a subject that is diagnosed with a metastatic melanoma may be administered one or more treatment modality (e.g., radiotherapy), and/or therapeutic agent including, but limited to, Bacille Calmaette-Guerin (BCG), interleukin-2 or other cytokine, imiquimod, or one or more chemotherapeutic agents (e.g., dacarbazine, Abraxane, BRAF or MEK or AKT inhibitors, and/or temozolomide), one or more immunotherapeutic agents (e.g., ipilimumab), or a combination thereof, i.e., a combination therapy such as administration of a chemotherapeutic agent (e.g., temozolomide and/or dacarbazine) in combination with interleukin, interferon, or both.

Other therapeutic agents that may be administered to a subject having melanoma or another cancer based on an expression level of linc00340 or a related variant may include one or more targeted therapies, chemotherapeutic agents or chemotherapeutic combination therapy regimens according to standard treatment protocols established by the FDA for a particular cancer.

Examples of targeted therapies that may be used in accordance with the methods described herein include, but are not limited to, selective estrogen receptor modulators (SERMs) (e.g., tamoxifen, toremifene and fulvestrant), aromatase inhibitors (anastrozole, exemestane and letrozole), kinase inhibitors (imatinib mesulate, dasatinib, nilotinib, lapatinib, gefitinib, erlotinib, temsirolimus and everolimus), growth factor receptor inhibitors (e.g., Trastuzumab, cetuximab and panitumumab), regulators of gene expression (vorinostat, romidepsin, bexarotene, alitretinoin and tretinoin), apoptosis inducers (bortezomib and pralatrezate), angiogenesis inhibitors (bevacizumab, sorafenib, sunitinib and pazopanib), antibodies that trigger a specific immune response by binding a cell-surface protein on lymphocytes (rituximab, alemtuzumab and ofatumumab), antibodies or other molecules that deliver toxic molecules specifically to cancer cells (tositumomab, ibritumomab tiuxetan, denileukin diftitox), cancer vaccines and gene therapy.

Examples of additional chemotherapeutic agents that may be used in accordance with the methods described herein include, but are not limited to, 13-cis-Retinoic Acid, 2-Chlorodeoxyadenosine, 5-Azacitidine, 5-Fluorouracil, 6-Mercaptopurine, 6-Thioguanine, actinomycin-D, adriamycin, aldesleukin, alemtuzumab, alitretinoin, all-transretinoic acid, alpha interferon, altretamine, amethopterin, amifostine, anagrelide, anastrozole, arabinosylcytosine, arsenic trioxide, amsacrine, aminocamptothecin, aminoglutethimide, asparaginase, azacytidine, bacillus calmette-guerin (BCG), bendamustine, bevacizumab, bexarotene, bicalutamide, bortezomib, bleomycin, busulfan, calcium leucovorin, citrovorum factor, capecitabine, canertinib, carboplatin, carmustine, cetuximab, chlorambucil, cisplatin, cladribine, cortisone, cyclophosphamide, cytarabine, darbepoetin alfa, dasatinib, daunomycin, decitabine, denileukin diftitox, dexamethasone, dexasone, dexrazoxane, dactinomycin, daunorubicin, decarbazine, docetaxel, doxorubicin, doxifluridine, eniluracil, epirubicin, epoetin alfa, erlotinib, everolimus, exemestane, estramustine, etoposide, filgrastim, fluoxymesterone, fulvestrant, flavopiridol, floxuridine, fludarabine, fluorouracil, flutamide, gefitinib, gemcitabine, gemtuzumab ozogamicin, goserelin, granulocyte—colony stimulating factor, granulocyte macrophage-colony stimulating factor, hexamethylmelamine, hydrocortisone hydroxyurea, ibritumomab, interferon alpha, interleukin-2, interleukin-4, interleukin-11, isotretinoin, ixabepilone, idarubicin, imatinib mesylate, ifosfamide, irinotecan, lapatinib, lenalidomide, letrozole, leucovorin, leuprolide, liposomal Ara-C, lomustine, mechlorethamine, megestrol, melphalan, mercaptopurine, mesna, methotrexate, methylprednisolone, mitomycin C, mitotane, mitoxantrone, nelarabine, nilutamide, octreotide, oprelvekin, oxaliplatin, paclitaxel, pamidronate, pemetrexed, panitumumab, PEG Interferon, pegaspargase, pegfilgrastim, PEG-L-asparaginase, pentostatin, plicamycin, prednisolone, prednisone, procarbazine, raloxifene, rituximab, romiplostim, ralitrexed, sapacitabine, sargramostim, satraplatin, sorafenib, sunitinib, semustine, streptozocin, tamoxifen, tegafur, tegafur-uracil, temsirolimus, temozolamide, teniposide, thalidomide, thioguanine, thiotepa, topotecan, toremifene, tositumomab, trastuzumab, tretinoin, trimitrexate, alrubicin, vincristine, vinblastine, vindestine, vinorelbine, vorinostat, or zoledronic acid.

Examples of known chemotherapeutic regimens may include, but are not limited to, ABVD, AC, BEACOPP, BEP, CA (or AC), CAF, CAV, CBV, ChIVPP/EVA, CHOP (or COHP), R-CHOP, COP (or CVP), CMF, COPP, EC, ECF, EP, EPOCH, FEC, FL (also known as Mayo), FOLFOX, FOLFIRI, ICE, ICE-R, m-BACOD, MACOP-B, MOPP, PCV, ProMACE-MOPP, ProMACE-CytaBOM, R-FCM, Stanford V, Thal/Dex, TIP, VAC, VAD, VAPEC-B, and VIP. Further explanation of these chemotherapeutic regimens is found in Table 1 below.

TABLE 1

Chemotherapeutic Regimens.

| Regimen | Components |
|---|---|
| ABVD | Adriamycin (doxorubicin), bleomycin, vinblastine, dacarbazine |
| AC | Adriamycin (doxorubicin), cyclophosphamide |
| BEACOPP | Bleomycin, etoposide, Adriamycin (doxorubicin), cyclophosphamide, Oncovin (vincristine), procarbazine, prednisone |
| BEP | Bleomycin, etoposide, platinum agent (cisplatin) |
| CA | Cyclophosphamide, Adriamycin (doxorubicin) (same as AC) |
| CAF | Cyclophosphamide, Adriamycin (doxorubicin), fluorouracil (5-FU) |
| CAV | Cyclophosphamide, Adriamycin (doxorubicin), vincristine |
| CBV | Cyclophosphamide, BCNU (carmustine), VP-16 (etoposide) |
| ChlVPP/EVA | Chlorambucil, vincristine (Oncovin), procarbazine, prednisone, etoposide, vinblastine, Adriamycin (doxorubicin) |
| CHOP or COHP | Cyclophosphamide, hydroxydoxorubicin (doxorubicin), vincristine (Oncovin), prednisone |
| CHOP-R or R-CHOP | CHOP + rituximab |
| COP or CVP | Cyclophosphamide, Oncovin (vincristine), prednisone |
| CMF | Cyclophosphamide, methotrexate, fluorouracil (5-FU) |
| COPP | Cyclophosphamide, Oncovin (vincristine), procarbazine, prednisone |
| EC | Epirubicin, cyclophosphamide |
| ECF | Epirubicin, cisplatin, fluorouracil (5-FU) |
| EP | Etoposide, platinum agent (cisplatin) |
| EPOCH | Etoposide, prednisone, Oncovin, cyclophosphamide, and hydroxydaunorubicin |
| FEC | Fluorouracil (5-FU), epirubicin, cyclophosphamide |
| FL (Also known as Mayo) | Fluorouracil (5-FU), leucovorin (folinic acid) |
| FOLFOX | Fluorouracil (5-FU), leucovorin (folinic acid), oxaliplatin |
| FOLFIRI | Fluorouracil (5-FU), leucovorin (folinic acid), irinotecan |
| ICE | ifosfamide, carboplatin, etoposide (VP-16) |
| ICE-R | ICE + rituximab |
| m-BACOD | Methotrexate, bleomycin, Adriamycin (doxorubicin), cyclophosphamide, Oncovin (vincristine), dexamethasone |
| MACOP-B | Methotrexate, leucovorin (folinic acid), Adriamycin (doxorubicin), cyclophosphamide, Oncovin (vincristine), prednisone, bleomycin |
| MOPP | Mechlorethamine, Oncovin (vincristine), procarbazine, prednisone |
| PCV | Procarbazine, CCNU (lomustine), vincristine |
| ProMACE- | Methotrexate, Adriamycin (doxorubicin), |

TABLE 1-continued

| Chemotherapeutic Regimens. | |
|---|---|
| Regimen | Components |
| MOPP | cyclophosphamide, etoposide + MOPP |
| ProMACE-CytaBOM | Prednisone, doxorubicin (adriamycin), cyclophosphamide, etoposide, cytarabine, bleomycin, Oncovin (vincristine), methotrexate, leucovorin |
| R-FCM | Rituximab, fludarabine, cyclophosphamide, mitoxantrone |
| Stanford V | Doxorubicin, mechlorethamine, bleomycin, vinblastine, vincristine, etoposide, prednisone |
| Thal/Dex | Thalidomide, dexamethasone |
| TIP | Paclitaxel, ifosfamide, platinum agent cisplatin |
| VAC | Vincristine, Actinomycin, Cyclophosphamide |
| VAD | Vincristine, Adriamycin (doxorubicin), dexamethasone |
| VAPEC-B | Vincristine, Adriamycin (doxorubicin), prednisone, etoposide, cyclophosphamide, bleomycin |
| VIP | Etoposide, ifosfamide, platinum agent cisplatin |

The methods described may be used alone or in combination with other methods for treating melanoma. For example if a subject has been diagnosed with a melanoma that tests positive for a BRAF gene mutation, the one or more agents described above may be combined with administration of a therapeutically effective amount of vemurafenib.

The term “effective amount” as used herein refers to an amount of a compound that produces a desired effect. For example, a population of cells may be contacted with an effective amount of a compound to study its effect in vitro (e.g., cell culture) or to produce a desired therapeutic effect ex vivo or in vitro. An effective amount of a compound may be used to produce a therapeutic effect in a subject, such as preventing or treating a target condition, alleviating symptoms associated with the condition, or producing a desired physiological effect. In such a case, the effective amount of a compound is a “therapeutically effective amount,” “therapeutically effective concentration” or “therapeutically effective dose.” The precise effective amount or therapeutically effective amount is an amount of the composition that will yield the most effective results in terms of efficacy of treatment in a given subject or population of cells. This amount will vary depending upon a variety of factors, including but not limited to the characteristics of the compound (including activity, pharmacokinetics, pharmacodynamics, and bioavailability), the physiological condition of the subject (including age, sex, disease type and stage, general physical condition, responsiveness to a given dosage, and type of medication) or cells, the nature of the pharmaceutically acceptable carrier or carriers in the formulation, and the route of administration. Further an effective or therapeutically effective amount may vary depending on whether the compound is administered alone or in combination with another compound, drug, therapy or other therapeutic method or modality. One skilled in the clinical and pharmacological arts will be able to determine an effective amount or therapeutically effective amount through routine experimentation, namely by monitoring a cell’s or subject’s response to administration of a compound and adjusting the dosage accordingly. For additional guidance, see Remington: The Science and Practice of Pharmacy, 21st Edition, Univ. of Sciences in Philadelphia (USIP), Lippincott Williams & Wilkins, Philadelphia, Pa., 2005, which is hereby incorporated by reference as if fully set forth herein.

The term “in combination” or “in combination with,” as used herein, means in the course of treating the same disease in the same patient using two or more agents, drugs, treatment regimens, treatment modalities or a combination thereof, in any order. This includes simultaneous administration, as well as in a temporally spaced order of up to several days apart. Such combination treatment may also include more than a single administration of any one or more of the agents, drugs, treatment regimens or treatment modalities. Further, the administration of the two or more agents, drugs, treatment regimens, treatment modalities or a combination thereof may be by the same or different routes of administration.

The term “subject” as used herein means a human or other mammal. In some embodiments, the subject may be a cancer patient (e.g., a melanoma patient).

In certain embodiments, modifications of the lncRNA transcript (which may be indicated herein as lncRNA transcripts “or modifications thereof”) may also be used as a biomarker for detecting, prognosing and monitoring cancer according to the methods described herein. Modifications or of lncRNA transcripts (i.e., lncRNA transcripts “or modifications thereof”) that may be detected and may be indicative of cancer when used according to the methods described herein may include, but are not limited to, single nucleotide polymorphisms (SNPs), DNA methylation or unmethylation (see Example 5 below), RNA methylation or unmethylation, and gene mutations or deletions. Such modifications may result in an alteration in the expression, formation, or conformation of the lncRNA transcript in a cancerous or biological sample, as compared to a control. For example, an lncRNA that contains one or more SNPs, one or more mutations, one or more deletions or a combination thereof within an exon may result in an alteration in the conformation of the lncRNA resulting in inhibition or impairment of an miRNA- or other sRNA-related silencing, thereby altering the amount of the lncRNA able to interact with cellular processes. Alternatively, an lncRNA that contains one or more SNPs, one or more mutations, one or more deletions or a combination thereof within an intronic region may result in an alteration in the splicing and expression of the lncRNA. Alternatively, downstream targets of the lncRNA transcript may be used as biomarkers for detecting, prognosing and monitoring cancer according to the methods described herein, Further, detection of the modifications discussed above may affect the ability to treat the cancer associated with said modification. For example, a specific mutation may be more responsive or resistant to a particular cancer therapy. Thus, if a subject having melanoma is determined to have a particular mutation, a therapeutic decision may be made with respect to the type of chemotherapeutics, targeted therapy or combination therapies that would be most effective in that subject. Alternatively, DNA or RNA methylation or unmethylation may also influence a therapeutic decision. For example, a patient that is determined to have a hypermethylated region of the lncRNA transcript may receive a demethylation agent (e.g., cytidine analogs such as azacitidine or decitabine) to induce lncRNA expression for the most effective treatment.

In certain other embodiments, the localization of an lncRNA transcript may be a biomarker that may be used in accordance with the methods described herein. For example, subcellular fractionation experiments were conducted and indicated that the linc00340 transcripts are present in both the cytoplasm and the nucleus of melanoma cells. Therefore, variations in the subcellular localization of linc00340 transcripts may be associated with a specific tumor stage (primary vs. metastatic) or outcome.

In some embodiments, the methods described herein may include a step of diagnosing a subject as having cutaneous melanoma when a test level of an lncRNA transcript or modification thereof is significantly different than a control level. A diagnosis may refer to the detection, determination, or recognition of a health status or condition of a subject. In certain embodiments, the diagnostic method may detect, determine, or recognize the presence or absence of melanoma cancer; prediction or diagnosis of metastasis or lack of metastasis, type or sub-type, or other classification or characteristic of melanoma cancer; whether a specimen is a benign lesion or a malignant tumor, or a combination thereof. In other embodiments, the methods described herein may also be used to differentiate between an early stage cancer (i.e., primary tumor); or a locoregional or distant metastasis when the test level is significantly different than the control level, or when the test level falls above or below a cutoff value (e.g., $25^{th}$ percentile, $50^{th}$ percentile (or median percentile), $75^{th}$ percentile).

The lncRNA transcript may be a transcript, variant transcript, or modification thereof that is part of the 6p22.3 genomic locus, which is amplified in metastatic melanoma and melanoma circulating tumor cells. The intergenic 6p22.3 region, which is between the SOX4 and PRL genes (nucleotide 21598851 to nucleotide 22287474), is transcribed into several long noncoding RNAs (lncRNAs) of different sizes. One such lncRNA is a linc00340 transcript (the "parent linc00340 transcript") (Gene ID: 401237). As described above, several variant transcripts of the linc00340 parent transcript have been shown to be differentially expressed in melanoma (linc00340v1 to linc00340v26; SEQ ID NO:1 to SEQ ID NO:26). Another such lncRNA is a LOC729177 transcript (Gene ID: 729177). According to one embodiment, the lncRNA transcript that may be used in accordance with the methods described herein is the linc00340 transcript and variants thereof (e.g., linc00340v1 to linc00340v26; SEQ ID NO:1 to SEQ ID NO:26). In another embodiment, the lncRNA transcript may be the LOC729177 transcript (Gene ID: 729177).

In other embodiments, the methods may also include a step of determining a prognosis for a subject having cutaneous melanoma when a test level of an lncRNA transcript or modification thereof is significantly different than a control level. The prognosis may refer to a prediction of a future course of a disease or condition in a subject who has the disease or condition (e.g., predicting patient survival), and may also encompass the evaluation of the response or outcome of the disease in the individual after administering a treatment or therapy to the individual. The prognosis may be a poor prognosis or a good prognosis, as measured by a decreased length of survival or a prolonged (or increased) length of survival, respectively. The prognosis may be further quantified by analyzing an associated Kaplan-Meyer curve, indicating a chance (or percent probability) of survival over a period of time. FIG. 6 shows Kaplan-Meyer curves that a test level from a patient sample may be compared to in order to predict the patient's probability for survival over a specific time period, e.g., 6 months, 1 year, 2 years, 3 years, 4 years, 5 years, or more than 5 years. Further, the survival may be measured as an overall survival (OS) or disease-free survival (DFS).

A biomarker, such as an lncRNA transcript or modification thereof that is differentially expressed or detected in a biological sample as described herein, may be a prognostic or a predictive marker. Prognostic and predictive biomarkers are distinguishable. A prognostic biomarker may be associated with a particular condition or disease, but is based on data that does not include a non-treatment or non-diseased control group. A predictive biomarker is associated with a particular condition or disease, as compared to a non-treated, non-diseased or other relevant control group (e.g., a different stage of cancer). By including such a control group, a prediction can be made about the prognosis of a patient that cannot be made using a prognostic biomarker.

In certain embodiments, the methods described herein may include a step of monitoring or assessing the progression of cutaneous melanoma in a subject; monitoring or assessing a response to treatment in a subject having cutaneous melanoma; monitoring or assessing a metastatic spread of melanoma in a subject; monitoring or assessing a remission state or a recurrence of melanoma in a subject or a combination thereof. Such monitoring or assessing may include an individual's response to a therapy, such as, for example, predicting whether an individual is likely to respond favorably to a therapeutic agent, is unlikely to respond to a therapeutic agent, or will likely experience toxic or other undesirable side effects as a result of being administered a therapeutic agent; selecting a therapeutic agent for administration to an individual, or monitoring or determining an individual's response to a therapy that has been administered to the individual.

A biological sample refers to any material, biological fluid, tissue, or cell obtained or otherwise derived from a subject including, but not limited to, blood (including whole blood, leukocytes, peripheral blood mononuclear cells, plasma, and serum), sputum, mucus, nasal aspirate, urine, semen, saliva, meningeal fluid, lymph fluid, milk, bronchial aspirate, a cellular extract, and cerebrospinal fluid. This also includes experimentally separated fractions of all of the preceding. For example, a blood sample can be fractionated into serum or into fractions containing particular types of blood cells, such as red blood cells or white blood cells (leukocytes). If desired, a sample may be a combination of samples from an individual, such as a combination of a tissue and fluid sample. A biological sample may also include materials containing homogenized solid material, such as from a stool sample, a tissue sample, or a tissue biopsy; or materials derived from a tissue culture or a cell culture.

A test value, expression level or other calculated test level of an lncRNA transcript, modification thereof, or other biomarker refers to an amount of a biomarker, such as an lncRNA transcript or modification thereof, in a subject's undiagnosed biological sample. The test level may be compared to that of a control sample, or may be analyzed based on a reference standard that has been previously established to determine a status of the sample. A test sample or test amount can be either in absolute amount (e.g., number of copies/ml, nanogram/ml or microgram/ml) or a relative amount (e.g., relative intensity of signals).

A control value, expression level or other calculated level of an lncRNA transcript, modification thereof, or other biomarker may be any amount or a range of amounts to be compared against a test amount of a biomarker. A control level may be the amount of a marker in a healthy or non-diseased state. For example, a control amount of a marker can be the amount of a marker in a population of patients with a specified condition or disease or a control population of individuals without said condition or disease. A control amount can be either in absolute amount (e.g., number of copies/ml, nanogram/ml or microgram/ml) or a relative amount (e.g., relative intensity of signals).

The test level of lncRNA transcript or modification thereof used in the methods for diagnosis, prognosis or monitoring melanoma cancer described may be measured, quantified and/or detected by any suitable RNA detection, quantification or sequencing methods known in the art, including, but not limited to, reverse transcriptase-polymerase chain reaction (RT-PCR) methods, microarray, serial analysis of gene expression (SAGE), next-generation RNA sequencing (e.g., deep sequencing, whole transcriptome sequencing, exome sequencing), gene expression analysis by massively parallel signature sequencing (MPSS), immune-derived colorimetric assays, situ hybridization (ISH) formulations (colorimetric/radiometric) that allow histopathology analysis, mass spectrometry (MS) methods, RNA pull-down and chromatin isolation by RNA purification (ChiRP), and proteomics-based identification (e.g., protein array, immunoprecipitation) of lncRNA. In one embodiment, the method of measuring an lncRNA transcript (or modification thereof) level includes performing quantitative/gel-based electrophoresis PCR or non-PCR-based molecular amplification methods for detection.

In some embodiments, the test level and the control level may be expressed as a mean comparative quantification (Cq) test value and a mean comparative quantification (Cq) control value (delta Cq method). In such a case, the mean Cq test value and a mean Cq control value are normalized by an internal control. For example, in tumor tissue (e.g., PEAT) samples, the difference of threshold cycle (Cq) values obtained for the target lncRNA (e.g., linc00340) and internal control in a cancer specimen was compared to the difference of the Cq values obtained in adjacent normal tissue. The delta-delta Cq method may then be used to calculate the relative expression values between tissue samples.

The methods described herein have been described as relating to cutaneous melanoma, however, additional lncRNA transcripts or modifications thereof may be used to diagnose, prognose or analyze any type of tumor or cancer. Cancers and tumor types that may be treated or attenuated using the methods described herein include but are not limited to bone cancer, bladder cancer, brain cancer, breast cancer, cancer of the urinary tract, carcinoma, cervical cancer, colon cancer, esophageal cancer, gastric cancer, hepatocellular carcinoma, head and neck cancer, hepatocellular cancer, lung cancer, lymphoma and leukemia, melanoma, neuroblastoma, ovarian cancer, pancreatic cancer, pituitary cancer, prostate cancer, rectal cancer, renal cancer, sarcoma, primary brain tumors, thyroid cancer, and uterine cancer. In addition, the methods may be used to treat tumors that are malignant (e.g., primary or metastatic cancers) or benign (e.g., hyperplasia, carcinoids, hematoma, and malignant potential nbenign neoplasms).

The following examples are intended to illustrate various embodiments of the invention. As such, the specific embodiments discussed are not to be construed as limitations on the scope of the invention. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entirety, as if fully set forth herein.

EXAMPLES

Example 1

The linc00340 Transcript is Overexpressed in Melanoma Cell Lines

Figure 1B:
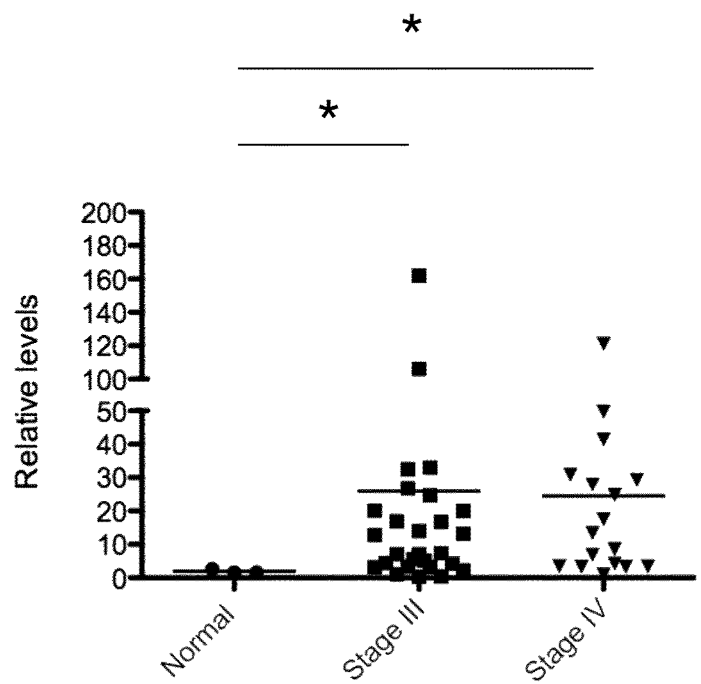

Using quantitative real-time PCR (qPCR), expression of linc00340 variants (v9) were measured in 3 normal melanocyte lines, 48 metastatic melanoma cell lines, 30 stage III melanoma cell lines, and 18 stage IV melanoma cell lines. Levels of linc00340 were normalized to SDHA housekeeping transcript levels using the delta-delta Cq method. As shown in FIG. 1A (*$p<0.05$; t-test), the linc00340 variant RNA was overexpressed in melanoma cells as compared to melanocytes (normal control). linc00340 RNA was also overexpressed in stage III and stage IV melanoma cells as compared to melanocytes (FIG. 1B; *$p<0.05$; Mann-Whitney-test). These results show that expression levels of linc00340 may be used to diagnose cutaneous melanoma, and may further be used to diagnose metastatic melanoma.

Figure 13:
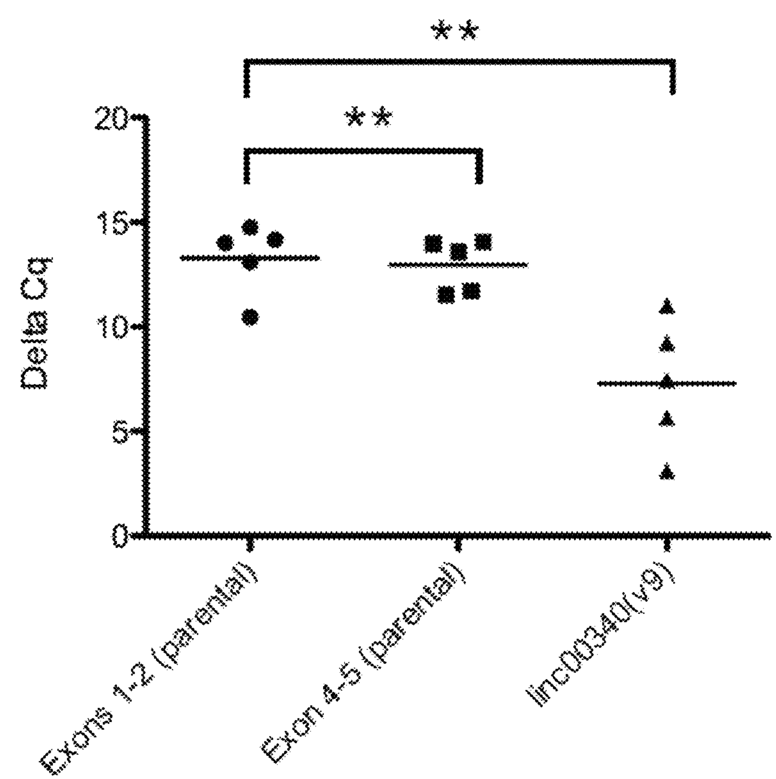
FIG. 13 shows that parental linc00340 is expressed in melanoma cell lines.

Parental linc00340 (exon 1-2 and exon 4-5) is also expressed in melanoma cell lines (n=4) (FIG. 13). The levels are significantly lower than linc00340(v9) ($p<0.01$) (FIG. 13**). The y-axis represents delta-Cq values using SDHA as a housekeeping gene (the higher the delta Cq, the lower the expression level). These lower parental linc00340 levels correlate with high methylation score of CpG sites located between nucleotide 21665716 and 21666862. Methylation levels were measured using the Illumina 450K Methylation Bead Array.

Example 2

Multiple linc00340 Splice variants are Expressed in Melanoma Cells

Figure 2A:
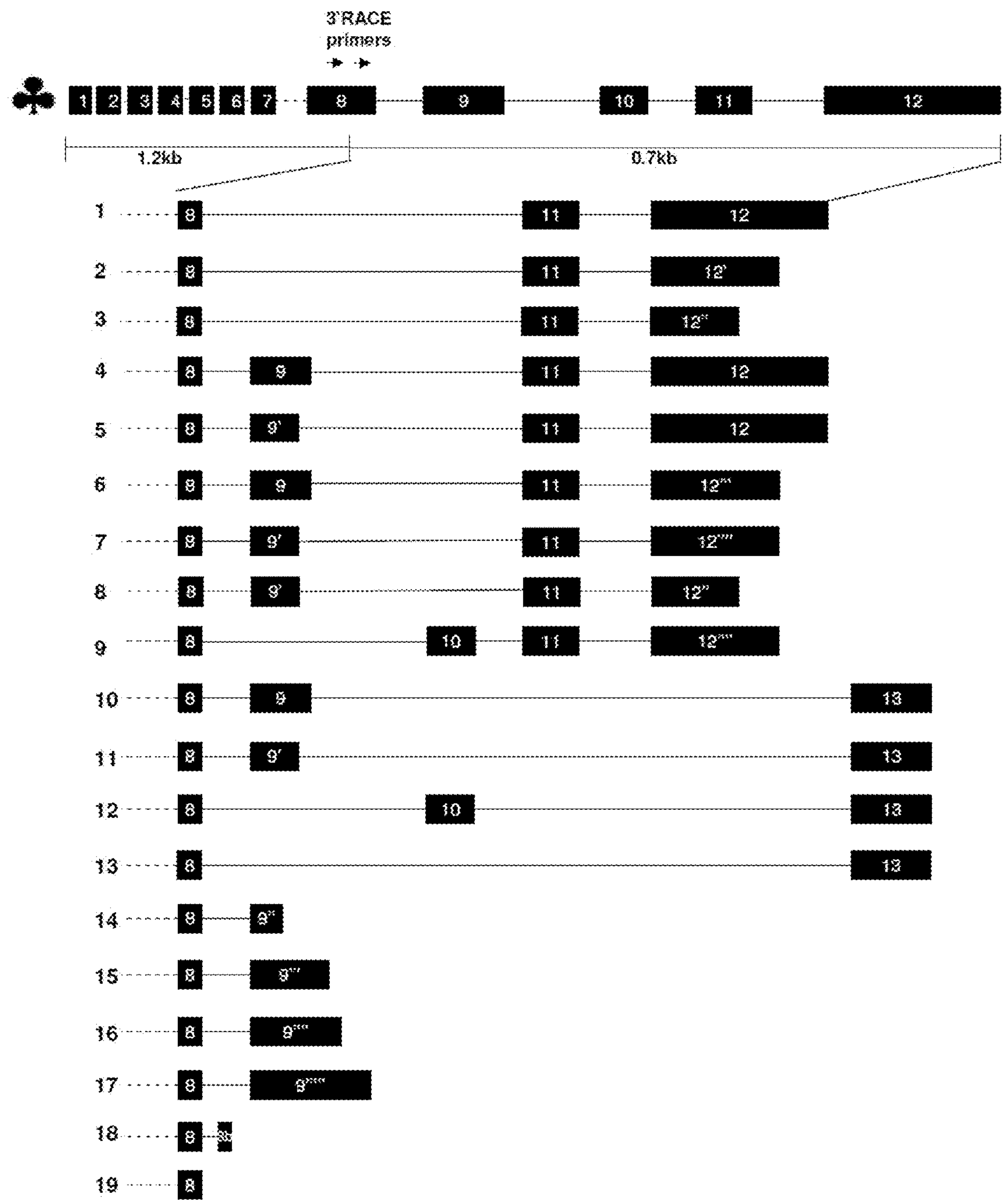
FIG. 2A is a schematic representation of multiple novel linc00340 splice variants expressed in melanoma cell lines.

Several novel linc00340 variants were identified, cloned and isolated using 3'-rapid amplification of cDNA ends (3' RACE; First Choice RLM-RACE kit, Life Technologies) targeting exon 8 of the 12-exon 1.9 kb parent linc00340 transcript (NCBI Gene ID: 401237; RefSeq ID: NR_015410.1). 3'RACE involves reverse transcription of RNA into cDNA using a 3'adapter, followed by 2 rounds of PCR amplification with nested primers. The forward primers (outer and inner) are gene-specific (eg.: Exon 8 of linc00340) and the reverse primers (outer and inner) are located with the 3'-adapter. Following PCR amplification, PCR products are purified, cloned, and sequenced using standard molecular biology techniques. FIG. 2A shows schematic diagrams of the new linc00340 variants (v1 to v19; SEQ ID NO:1 to SEQ ID NO:19, respectively) expressed in melanoma cells. The new variants are shown below a schematic of the parent transcript. The sequence of these isolated variants is shown in FIG. 8.

Figure 2B:
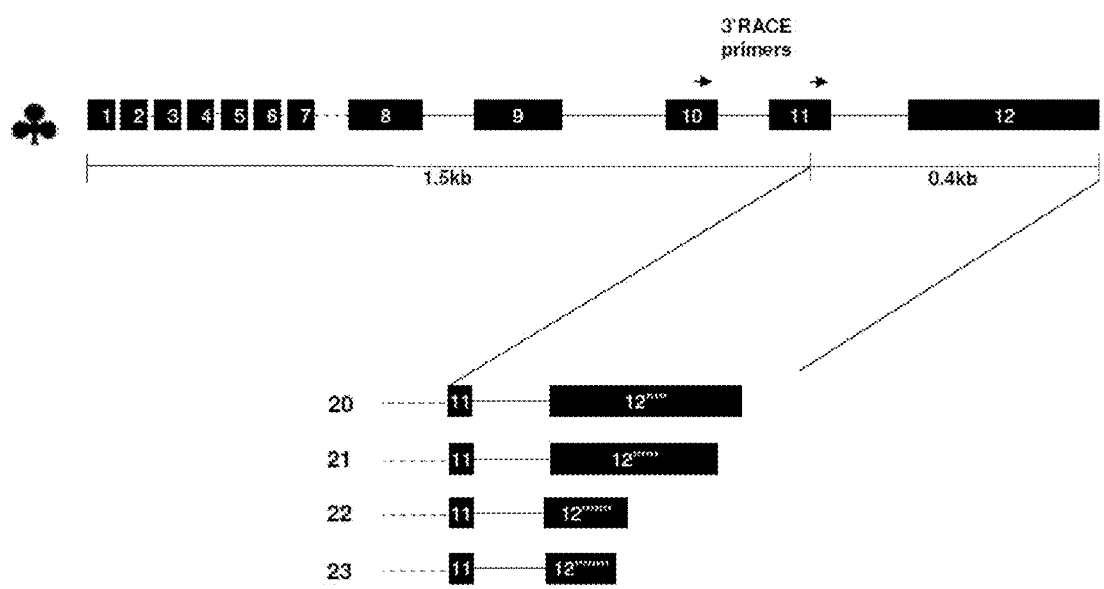
FIG. 2B shows variants linc00340v20 to linc00340v23 (SEQ ID NO:20 to SEQ ID NO:23, respectively) that were cloned using 3'-rapid amplification of cDNA ends (3' RACE) using primers targeting exons 10-11 of the parent linc00340 transcript (top ♣).

Additional novel linc00340 variants were identified, cloned and isolated using 3'-rapid amplification of cDNA ends (3' RACE) targeting exons 10-11 of the 12-exon 1.9 kb parent linc00340 transcript (NCBI Gene ID: 401237; RefSeq ID: NR_015410.1). FIG. 2B shows schematic diagrams of the new linc00340 variants (v20 to v23; SEQ ID NO:20 to SEQ ID NO:23, respectively) expressed in melanoma cells. These variants are shown below a schematic of the parent transcript. The sequence of these isolated variants is shown in FIG. 9.

Example 3

Figure 3:
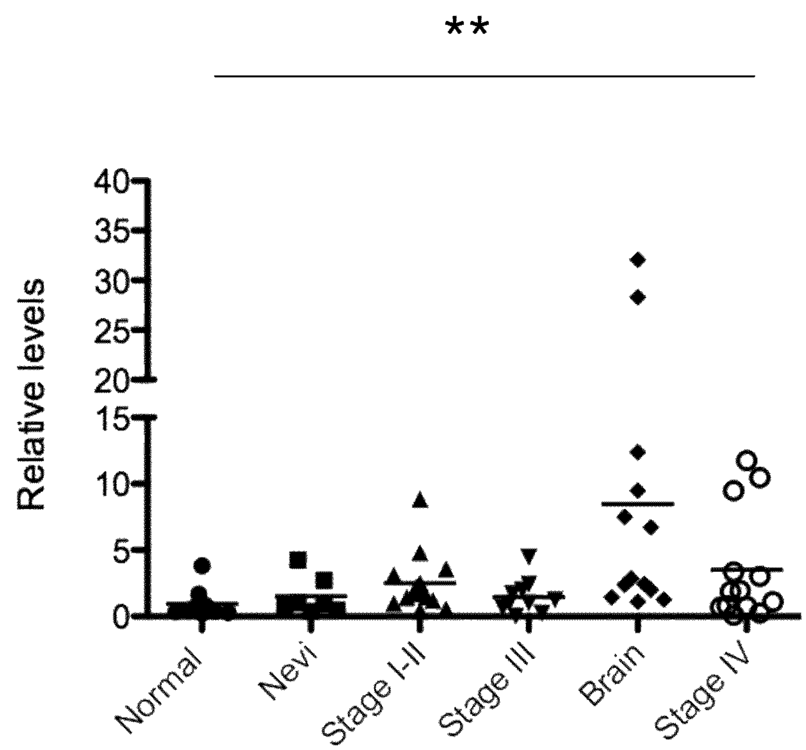
FIG. 3 illustrates that tissue expression of linc00340 RNA correlates with melanoma progression. Expression of linc00340 increased significantly from normal skin and nevi to stage IV melanoma (**$p=0.005$; Kruskal-Wallis test). Horizontal bars indicate the mean. Levels of linc00340 were normalized to SDHA housekeeping transcript levels using the delta-delta Cq method.

Tissue Expression of linc00340 Variants Correlates with Melanoma Progression Using qPCR, expression of a linc00340 variant (v9) transcript was measured in normal skin tissue (n=10), nevi tissue (n=7), melanoma stage 1-11 cancer tissue (n=14), melanoma stage III cancer tissue (n=10), and melanoma stage IV cancer tissue (n=26). As shown in FIG. 3, expression of the linc00340 variant increases significantly from normal skin and nevi to stage IV melanoma ($p=0.005$; Kruskal-Wallis test). Levels of the linc00340 were normalized to SDHA housekeeping transcript levels using the delta-delta Cq method. The expression of the linc00340 RNA shows a trend of increasing with melanoma progression from normal skin and nevi to stage IV disease (FIG. 3). Further, the expression of the linc00340 RNA was particularly elevated in melanoma brain metastases, showing a high expression of linc00340 in 6 out 13 (46%) of brain metastatic melanoma tumors (FIG. 3**).

Using qPCR, expression of linc00340 variants was measured in non-cancer tissue (n=15), primary melanoma tumors (n=22), and metastatic melanoma tissues (n=38), (FIG. 4). In FIG. 4A, expression of linc00340(v1-19) increases significantly from non-cancer to primary and metastatic melanoma ($p=0.05$; One-way ANOVA). The levels of linc00340(v1-19) are significantly increased in both primary and metastatic melanoma as compared to non-cancer tissues (**$p<0.01$ and *$p<0.05$, respectively, t-test). In FIG. 4B, expression of linc00340(v9) increases significantly from non-cancer to primary and metastatic melanoma ($p=0.02$; One-way ANOVA). The levels are linc00340(v1-19) are also significantly increased in both primary and metastatic melanoma compared to non-cancer tissues (**$p<0.01$ and *$p<0.05$, respectively, t-test). Levels of linc00340 were normalized to SDHA housekeeping transcript levels using the delta-delta Cq method.

Example 4

Figure 5:
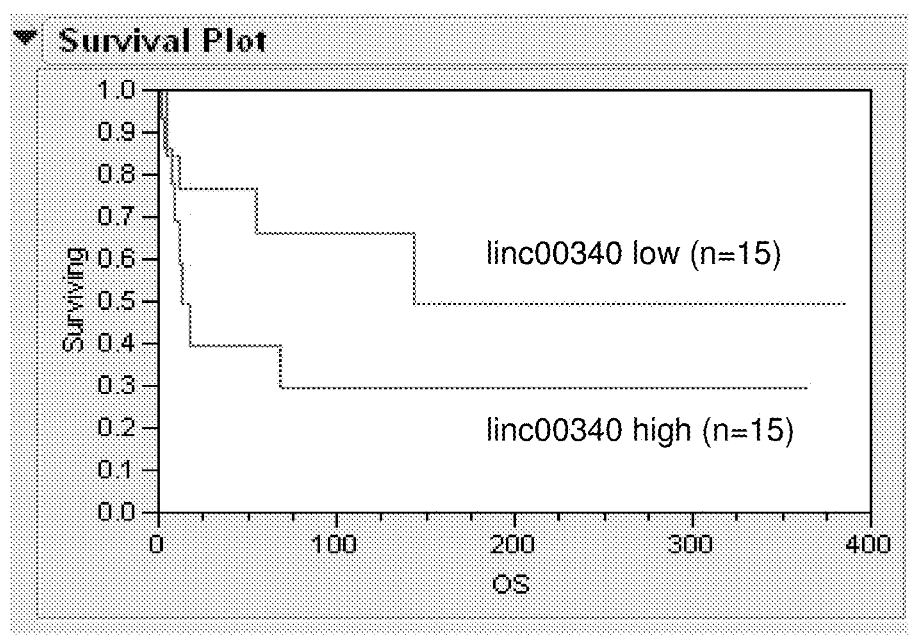
FIG. 5 is a Kaplan-Meier curve illustrating that high levels of linc00340 are correlated with shorter survival. A trend towards shorter survival in cell lines expressing high levels (above median) of linc00340 was observed (Log Rank p value=0.18)

Expression of linc00340 and linc00340 Variants is Associated with Patient Survival Expression of linc00340 in Melanoma Cell Lines Melanoma cell lines derived from stage III melanoma patients were divided into two groups: those expressing high levels (i.e., above the $50^{th}$ percentile or median) of linc00340 (v9) ("linc00340 high") and those expressing low levels (below the $50^{th}$ percentile or median) of linc00340(v9) ("linc00340 low"). These groups were analyzed by a Kaplan-Meier curve depicting the overall survival of stage III melanoma patients with respect to linc00340 transcript levels in the corresponding stage III cell lines. (FIG. 5). As shown in FIG. 5, the linc00340 high group (n=15) showed a poor prognosis as compared to the linc00340 low group (n=15). This suggests that later stage melanoma patients (i.e., stage III or IV) that have a high level of linc00340 expression will likely have a poor prognosis, and will likely have a shorter overall survival as compared to later stage melanoma patients (i.e., stage III or IV) that have a low level of linc00340 expression, who likely have a good prognosis or better prognosis and a longer overall survival. Because cell culture data is not always indicative of clinical results using tissue samples, these results were then compared to similar experiments using harvested tissue samples as described below.

Expression of linc00340 Variants in Primary and Metastatic Specimens is Associated with Patient Survival In FIG. 6A, primary melanoma specimens were divided into 2 groups according to linc00340(v1-19) expression: those expressing high levels (>$25^{th}$ percentile) and those expressing low levels (<$25^{th}$ percentile). These groups were analyzed by a Kaplan-Meier curve depicting the overall survival of the corresponding patients. The linc00340(v1-19) high group (n=15) showed a poor prognosis as compared to the linc00340(v1-19) low group (n=5). This suggests that patients with high level of linc00340(v1-19) expression in their primary tumor will likely have a poor prognosis, and will likely have a shorter overall survival as compared to patients that have a low level of linc00340(v1-19) expression in their primary tumor, who likely have a good prognosis or better prognosis and a longer overall survival (Log Rank 3.9; $p<0.05$). Levels of linc00340 were normalized to SDHA housekeeping transcript levels using the delta-delta Cq method.

In FIG. 6B, metastatic melanoma specimens were divided into 2 groups according to linc00340(v9) expression: those expressing high levels (>median) and those expressing low levels (<median). These groups were analyzed by a Kaplan-Meier curve depicting the overall survival of the corresponding patients. The linc00340(v9) low group (n=16) showed a poor prognosis as compared to the linc00340(v9) high group (n=17). This suggests that patients with low level of linc00340(v9) expression in their metastatic tumor will likely have a poor prognosis, and will likely have a shorter overall survival as compared to patients that have a high level of linc00340(v9) expression in their metastatic tumor, who likely have a good prognosis or better prognosis and a longer overall survival (Log Rank 8.5, $p<0.005$). Levels of linc00340 were normalized to SDHA housekeeping transcript levels using the delta-delta Cq method.

Example 5

Tissue Expression of linc00340 Variant Inversely Correlated with DNA Methylation FIG. 7A represents the linc00340 alternative transcription start sites (TSS) and linc00340 variants expressed in melanoma cells that were identified using 5'-rapid amplification of cDNA ends (5'-RACE); First Choice RLM-RACE kit, Life Technologies) that targets exon 8. 5'RACE involves the ligation of a 5'adapter to RNA and reverse transcription of the RNA into cDNA using random primers and/or oligo-dt primers. This is followed by 2 rounds of PCR amplification with nested primers. The forward primers (outer and inner) are located within the 5'adapter and the reverse primers (outer and inner) are gene-specific (eg.: Exon 8 of linc00340). Following PCR amplification, PCR products are purified, cloned, and sequenced using standard molecular biology techniques. Variants 24 to 26 are shown below the predicted 12-exon 1.9 kb transcript (NCBI Gene ID: 401237; RefSeq ID: NR_015410.1). This figure illustrates the discovery of new TSS for linc00340 variant expression. The sequences of these variants are shown in FIG. 10.

FIG. 7B depicts the inverse correlation between CpG site DNA methylation within the new TSS and linc00340(v24-26) expression. Whole genome methylation analysis of 8 melanoma cell lines was performed using the Illumina 450K Illumina Methylation Bead Array. The methylation score of the cg15541384 probe located within the newly identified TSS was compared to linc00340(v24-26) expression levels (raw Cq values; the higher the Cq value, the lower the expression level). Results show that cg15541384 DNA methylation is inversely correlated with linc00340(v24-26) expression ($R^2=0.96$). This in turn demonstrates that DNA methylation can be a surrogate for linc00340 expression; high DNA methylation is indicative of low linc00340 expression, while low DNA methylation is indicative of high linc00340 expression.

It is noted that the exon 8 3'RACE and 5'RACE experiments performed in the examples above were done with overlapping primers. This means that at least 19 (3'RACE)×3 (5'RACE)=57 variants may actually exist, which illustrates the breadth of these variant transcripts.

REFERENCES

The references, patents and published patent applications listed below, and all references cited in the specification above are hereby incorporated by reference in their entirety, as if fully set forth herein.

Gibb E A, Brown C J, Lam W L. *The functional role of non-coding RNA in human carcinomas*. Molecular Cancer, 2011, 10:38.

Presner J R, Chinnaiyan A M. *The emergence of lncRNAs in cancer biology*. Cancer Discovery, 2011, 1(5): 391-407.

Wang K C, Chang H Y. *Molecular mechanisms of long non-coding RNAs*. Molecular Cell, 2011 Sep. 16; 43(6): 904-14.

Ryan C M, Robles A I and Harris C C. *Genetic variation in microRNA networks: the implications for cancer research*. Nature Cancer Reviews, 2010; 10:389-402. Maris J M, Masse Y P, Bradfield J P, HouC, Manni S, Scott R H, Asgharzadeh S, et al. *Chromosome 6p22 Locus Associated with Clinically Aggressive Neuroblastoma*. NEJM, 2008; 358:2585-2593.

Jia G, Fu Y, Shao X, Dai Q, Zheng G, Yang Y, Yi C, Lindahl T, PanT, Yan YG, and He C. *N6-Methyladenosine in nuclear RNA is a major substrate of the obesity-associated FTO*. Nature Chemical Biology, 2011; 7:885-887.

Verhaegh G W, Verkliej L, Vermeulen S H H M, den Heijer M, Witjes J A, Kiemeney L A. *Polymorphisms in the H19 Gene and the Risk of Bladder Cancer*. European Urology, 2008; 54:1118-1126.

Motorin Y, Lyko F and Helm M. 5-*methylcytosine in RNA: detection, enzymatic formation and biological functions*. 2009; 38:1415-1430.

International Patent Application Publication No WO/2009/046118, filed Oct. 1, 2008.

What is claimed is:

1. A method of treating a metastatic or primary cancer in a subject, comprising:

isolating one or more lncRNA transcripts in a biological sample from the subject, wherein the one or more isolated lncRNA transcripts are lnc00340 variant transcripts having a nucleotide sequence selected from SEQ ID NO:1-26;

measuring a test level of the one or more isolated lncRNA transcripts;

comparing the test level to a control level of the one or more lncRNA transcripts;

diagnosing a subject as having the cancer when the test level is higher than the control level; and treating the subject diagnosed with the cancer with a therapeutic effective dose of an agent inhibiting an lnc00340 transcript or the lnc00340 variant transcripts, wherein the agent is a nucleic acid.

2. The method of claim 1, wherein the biological sample is a cancer tissue sample.

3. The method of claim 1, wherein the cancer is cutaneous melanoma.

4. The method of claim 3, wherein the cutaneous melanoma is a metastatic melanoma.

5. The method of claim 1, wherein the test level of the one or more lncRNA transcripts are detected using reverse transcriptase-polymerase chain reaction (RTPCR) methods, quantitative real-time PCR (qPCR), microarray, serial analysis of gene expression (SAGE), next-generation RNA sequencing (deep sequencing), gene expression analysis by massively parallel signature sequencing (MPSS), immunoassays such as ELISA, in situ hybridization (ISH) formulations that allow histopathological analysis, mass spectrometry (MS) methods, transcriptomics, RNA pull-down and chromatin isolation by RNA purification (ChiRP), proteomics-based identification of lncRNA., detection of single nucleotide polymorphisms (SNPs), measurement of DNA methylation or unmethylation, measurement of siRNA silencing, or measurement of downstream targets.

6. The method of claim 1, wherein the agent inhibiting the lnc00340 transcript or the lnc00340 variant transcript is an antisense RNA, an RNA interference (RNAi) molecule, a decoy molecule, or an RNA aptamer.

7. The method of claim 6, wherein the RNAi molecule is an siRNA molecule, an esiRNA molecule, an shRNA molecule, or an miRNA molecule.

8. The method of claim 1, further comprising treating the subject diagnosed with the cancer with a therapeutic effective dose of imiquimod or an interferon.

9. A method of treating a metastatic or primary cancer in a subject, comprising:

isolating one or more lncRNA transcripts in a biological sample from the subject, wherein the one or more isolated lncRNA transcripts have a nucleotide sequence selected from SEQ ID NO:1-26;

measuring a test level of the one or more isolated IncRNA transcripts;

comparing the test level to a control level of the one or more IncRNA transcripts;

diagnosing a subject as having the cancer when the test level is higher than the control level; and treating the subject diagnosed with the cancer with a therapeutic effective dose of (i) a nucleic acid agent inhibiting the one or more isolated IncRNA transcripts, and (ii) imiquimod or an interferon.

10. The method of claim 9, wherein the biological sample is a cancer tissue sample.

11. The method of claim 9, wherein the cancer is cutaneous melanoma.

12. The method of claim 11, wherein the cutaneous melanoma is a metastatic melanoma.

13. The method of claim 9, wherein the test level of the one or more IncRNA transcripts are detected using reverse transcriptase-polymerase chain reaction (RTPCR) methods, quantitative real-time PCR (qPCR), microarray, serial analysis of gene expression (SAGE), next-generation RNA sequencing (deep sequencing), gene expression analysis by massively parallel signature sequencing (MPSS), immunoassays such as ELISA, in situ hybridization (ISH) formulations that allow histopathological analysis, mass spectrometry (MS) methods, transcriptomics, RNA pull-down and chromatin isolation by RNA purification (ChiRP), proteomics-based identification of IncRNA., detection of single nucleotide polymorphisms (SNPs), measurement of DNA methylation or unmethylation, measurement of siRNA silencing, or measurement of downstream targets.

* * * * *

SEQUENCE LISTING

```
<160> NUMBER OF SEQ ID NOS: 27

<210> SEQ ID NO 1
<211> LENGTH: 480
<212> TYPE: DNA
<213> ORGANISM: Artificial Sequence
<220> FEATURE:
<223> OTHER INFORMATION: Synthetic construct: linc00340v1

<400> SEQUENCE: 1

atgagtgagg atcaatggga agaagagagc cagccagttc tggagaccag aaggccaaaa     60

tcaaaagtat gggcaggctt gatttcttta gaagactcca gcggagaact gtgtctcctt    120

gcttctgatt ctacatctcc atccatgggc cactgtttca gcaacctcag ccagtgcaac    180

acaacctcag ccaagaagag tatgcagaga aaggagtccc ctacctgcca caaaactgtt    240

gtctgaaaac tgtctcatat tgcctcaagt tgtcattcat tgtgaattag acctgtttaa    300

catgtaatct gcaacatgct tcactgtcta attttccaga gcccctcata taaggaactg    360

tattattggt ataatcatca tggtgaagaa gttggtatgt gggggagaga tgacagaaac    420

agagagtaag tcagagctgg ctgcctgaca gataaaaagg aaatgaccaa aaaaaaaaaa    480


<210> SEQ ID NO 2
<211> LENGTH: 318
<212> TYPE: DNA
<213> ORGANISM: Artificial Sequence
<220> FEATURE:
<223> OTHER INFORMATION: Synthetic construct: linc00340v2

<400> SEQUENCE: 2

atgagtgagg atcaatggga agaagagagc cagccagttc tggagaccag aaggccaaaa     60

tcaaaagtat gggcaggctt gatttcttta gaagactcca gcggagaact gtgtctcctt    120

gcttctgatt ctacatctcc atccatgggc cactgtttca gcaacctcag ccagtgcaac    180

acaacctcag ccaagaagag tatgcagaga aaggagtccc ctacctgcca caaaactgtt    240

gtctgaaaac tgtctcatat tgtctcaagt tgtcattcat tgtgaattag acctgtttaa    300

catacaaaaa aaaaaaaa                                                  318


<210> SEQ ID NO 3
<211> LENGTH: 465
<212> TYPE: DNA
<213> ORGANISM: Artificial Sequence
<220> FEATURE:
<223> OTHER INFORMATION: Synthetic construct: linc00340v3

<400> SEQUENCE: 3

atgagtgagg atcaatggga agaagagagc cagccagttc tggagaccag aaggccaaaa     60

tcaaaagtat gggcaggctt gatttcttta gaagactcca gcggagaact gtgtctcctt    120
```

```
gcttctgatt ctacatctcc atccatgggc cactgtttca gcaacctcag ccagtgcaac    180

acaacctcag ccaagaagag tatgcagaga aaggagtccc ctacctgcca caaaactgtt    240

gtctgaaaac tgtctcatat tgtctcaagt tgtcattcat tgtgaattag acctgtttaa    300

catgtaatct gcaacatgct tcactgtcta attttccaga gcccctcata taaggaactg    360

tattattggt ataatcatca tggtgaagaa gttggtatgt gggggagaga tgacagaaac    420

agagagaaag tcggagctgg ctgcctgaca gacaaaaaaa aaaaa                    465
```

<210> SEQ ID NO 4
<211> LENGTH: 654
<212> TYPE: DNA
<213> ORGANISM: Artificial Sequence
<220> FEATURE:
<223> OTHER INFORMATION: Synthetic construct: linc00340v4

<400> SEQUENCE: 4

```
atgagtgagg atcaatggga agaagagagc cagccaggaa gttgaagatt tgtccaggag     60

cagatagccg aagagagaga gagagaagag agaacggctt acagctcagg tcctctctcc    120

atgcttagga accactacaa atgctactgc cttgagtctc attttgtttc cctctggaaa    180

ccacatgtgt accttgtttg caacagtatg ggtatggaga ccagaaggcc aaaatcaaaa    240

gtatgggcag gcttgatttc tttagaaggc tccagcggag aactgtgtct ccttgcttct    300

gattctacat ctccatccat gggccactgt ttcagcaacc tcagccagtg caacacaacc    360

tcagccaaga agagtatgca gagaaaggag tcccctacct gccacaaaac tgttgtctga    420

aaactgtctc atattgtctc aagttgtcat tcattgtgaa ttagacctgt ttaacatgta    480

atctgcaaca tgcttcactg tctaattttc cagagcccct catataagga actgtattat    540

tggtataatc atcatggtga agaagttggt atgtggggga gagatgacag aaacagagag    600

taagtcagag ctggctgcct gacagataaa aaggaaatga ccaaaaaaaa aaaa           654
```

<210> SEQ ID NO 5
<211> LENGTH: 553
<212> TYPE: DNA
<213> ORGANISM: Artificial Sequence
<220> FEATURE:
<223> OTHER INFORMATION: Synthetic construct: linc00340v5

<400> SEQUENCE: 5

```
atgagtgagg atcaatggga agaagagagc cagccaggaa gttgaagatt tgtccaggag     60

cagatagctg aagagagaga gagagaagag agaacggctt gcagctcagt tctggagacc    120

agaaggccaa aatcaaaagt atgggcaggc ttgatttctt tagaagactc cagcggagaa    180

ctgtgtctcc ttgcttctga ttctacatct ccatccatgg gccactgttt cagcaacctc    240

agccagtgca acacaacctc agccaagaag agtatgcaga gaaaggagtc ccctacctgc    300

cacaaaactg ttgtctgaaa actgtctcat attgtctcaa gttgtcattc attgtgaatt    360

agacctgttt aacatgtaat ctgcaacatg cttcactgtc taattttcca gagcccctca    420

tataaggaac tgtattattg gtataatcat catggtgaag aagttggtat gtgggggaga    480

gatgacagaa acagagggta agtcagagct ggctgcctga cagataaaaa ggaaatgacc    540

aaaaaaaaaa aaa                                                       553
```

<210> SEQ ID NO 6
<211> LENGTH: 391
<212> TYPE: DNA
<213> ORGANISM: Artificial Sequence

```
<220> FEATURE:
<223> OTHER INFORMATION: Synthetic construct: linc00340v6

<400> SEQUENCE: 6

atgagtgagg atcaatggga agaagagagc cagccaggaa gttgaagatt tgtccaggag     60

cagatagctg aagagagaga gagagaagag agaacggctt acagctcagt tctggagacc    120

agaaggccaa aatcaaaagt atgggcaggc ttgatttctt tagaagactc cagcggagaa    180

ctgtgtctcc ttgcttctga ttctacatct ccatccatgg gccactgttt cagcaacctc    240

agccagtgca acacaacctc agccaagaag agtatgcaga gaaaggagtc ccctacctgc    300

cacaaaactg ttgtctgaaa actgtctcat attgtctcaa gttgtcattc attgtgaatt    360

agacctgttt aacatgtaaa aaaaaaaaaa a                                  391


<210> SEQ ID NO 7
<211> LENGTH: 397
<212> TYPE: DNA
<213> ORGANISM: Artificial Sequence
<220> FEATURE:
<223> OTHER INFORMATION: Synthetic construct: linc00340v7

<400> SEQUENCE: 7

atgagtgagg atcaatggga agaagagagc cagccaggaa gttgaagatt tgtccaggag     60

cagatagctg aagagagaga gagagaagag agaacggctt acagctcagt tctggagacc    120

agaaggccaa aatcaaaagt atgggcaggc ttgatttctt tagaagactc cagcggagaa    180

ctgtgtctcc ttgcttctga ttctacatct ccatccatgg gccactgttt cagcaacctc    240

agccagtgca acacaacctc agccaagaag agtatgcaga gaaaggagtc ccctacctgc    300

cacaaaactg ttgtctgaaa actgtctcat attgtctcaa gttgtcattc attgtgaatt    360

agacctgttt aacatgtaat ctgcaaaaaa aaaaaaa                            397


<210> SEQ ID NO 8
<211> LENGTH: 537
<212> TYPE: DNA
<213> ORGANISM: Artificial Sequence
<220> FEATURE:
<223> OTHER INFORMATION: Synthetic construct: linc00340v8

<400> SEQUENCE: 8

atgagtgagg atcaatggga agaagagagc cagccaggaa gttgaagatt tgtccaggag     60

cagatagctg aagagagaga gagagaagag agaacggctt acagctcagt tctggagacc    120

agaaggccaa aatcaaaagt atgggcaggc ttgatttctt tagaagactc cagcggagaa    180

ctgtgtctcc ttgcttctga ttctacatct ccatccatgg gccactgttt cagcaacctc    240

agccagtgca acacaacctc agccaagaag agtatgcaga gaaaggagtc ccctacctgc    300

cacaaaactg ttgtctgaaa actgtctcat attgtctcaa gttgtcattc attgtgaatt    360

agacctgttt aacatgtaat ctgcaacatg cttcactgtc taattttcca gagcccctca    420

tataaggaac tgtattattg gtataatcat catggtgaag aagttggtat gtgggggaga    480

gatgacagaa acagagagaa agtcagagct ggctgcctga cagacaaaaa aaaaaaa      537


<210> SEQ ID NO 9
<211> LENGTH: 390
<212> TYPE: DNA
<213> ORGANISM: Artificial Sequence
<220> FEATURE:
<223> OTHER INFORMATION: Synthetic construct: linc00340v9
```

<400> SEQUENCE: 9

```
atgagtgagg atcaatggga agaagagagc cagccaggct cacaggcaga aggaattttc     60

cttgtcttgg atgagacttt tgacttggac ttttgggtta agttctggag accagaaggc    120

caaaatcaaa agtatgggca ggcttgattt ctttagaaga ctccagcgga gaactgtgtc    180

tccttgcttc tgattctaca tctccatcca tgggccactg tttcagcaac ctcagccagt    240

gcaacacaac ctcagccaag aagagtatgc agagaaagga gtcccctacc tgccacaaaa    300

ctgttgtctg aaaactgtct catattgtct caagttgtca ttcattgtga attagacctg    360

tttaacatgt aatctgcaaa aaaaaaaaaa                                     390
```

<210> SEQ ID NO 10
<211> LENGTH: 421
<212> TYPE: DNA
<213> ORGANISM: Artificial Sequence
<220> FEATURE:
<223> OTHER INFORMATION: Synthetic construct: linc00340v10

<400> SEQUENCE: 10

```
atgagtgagg atcaatggga agaagagagc cagccaggaa gttgaagatt tgtccaggag     60

cagatagctg aagagagaga gagagaagag agaacggctt acagctcagg tcctctcccc    120

atgcttagga accactacaa atgctactgc cttgagtctc attttgtttc cctctggaaa    180

ccacatgtgt accttgtttg caacagtatg gggcaccgag gaagagaacc aatggcagag    240

gccacatgtg caagcaagat gggagtctgg agagcctcag gctaaatcac gagtgctcag    300

ccctctcctc tttgtaaggg caaccgggtc atatctgcca gcatagaact gctctgtcca    360

cagccctaaa atctaatacc tagaacaata aatgcactta agcacgtcaa aaaaaaaaaa    420

a                                                                    421
```

<210> SEQ ID NO 11
<211> LENGTH: 318
<212> TYPE: DNA
<213> ORGANISM: Artificial Sequence
<220> FEATURE:
<223> OTHER INFORMATION: Synthetic construct: linc00340v11

<400> SEQUENCE: 11

```
atgagtgagg atcaatggga agaagagagc cagccaggaa gttgaagatt tgtccaggag     60

cagatagctg aagagagaga gagagaagag agaacggctt acagctcagg gcaccgagga    120

agagaaccaa tggcagaggc cacatgtgca agcaagatgg gagtctggag agcctcaggc    180

taaatcacga gtgctcagcc ctctcctctt tgtaagggca accgggtcat atctgccagc    240

atagaactgc tctgtccaca gccctaaaat ctaataccta gaacaataaa tgcacttaag    300

cacgtaaaaa aaaaaaaa                                                  318
```

<210> SEQ ID NO 12
<211> LENGTH: 311
<212> TYPE: DNA
<213> ORGANISM: Artificial Sequence
<220> FEATURE:
<223> OTHER INFORMATION: Synthetic construct: linc00340v12

<400> SEQUENCE: 12

```
atgagtgagg atcaatggga agaagagagc cagccaggct cacaggcaga aggaattttc     60

cttgtcttgg atgagacttt tgacttggac ttttgggtta agggcaccga ggaagagaac    120

caatggcaga ggccacatgt gcaagcaaga tgggagtctg gagagcctca ggctaaatca    180
```

```
cgagtgctca gccctctcct ctttgtaagg gcaaccgggt catatctgcc agcatagaac    240

tgctctgtcc acagccctaa aatctaatac ctagaacaat aaatgcactt aagcacgtca    300

aaaaaaaaaa a                                                         311


<210> SEQ ID NO 13
<211> LENGTH: 247
<212> TYPE: DNA
<213> ORGANISM: Artificial Sequence
<220> FEATURE:
<223> OTHER INFORMATION: Synthetic construct: linc00340v13

<400> SEQUENCE: 13

atgagtgagg atcaatggga agaagagagc cagccagggc accgaggaag agaaccaatg     60

gcagaggcca catgtgcaag caagatggga gtctggagag cctcaggcta aatcacgagt    120

gctcagccct ctcctctttg taagggcaac cgggtcatat ctgccagcat agaactgctc    180

tgtccacagc cctaaaatct aatacctaga acaataaatg cacttaagca cgtcaaaaaa    240

aaaaaaa                                                              247


<210> SEQ ID NO 14
<211> LENGTH: 94
<212> TYPE: DNA
<213> ORGANISM: Artificial Sequence
<220> FEATURE:
<223> OTHER INFORMATION: Synthetic construct: linc00340v14

<400> SEQUENCE: 14

atgagtgagg atcaatggga agaagagagc cagccaggaa gttgaagatt tgtccaggag     60

cagatagctg aagagggaga gaaaaaaaaa aaaa                                 94


<210> SEQ ID NO 15
<211> LENGTH: 240
<212> TYPE: DNA
<213> ORGANISM: Artificial Sequence
<220> FEATURE:
<223> OTHER INFORMATION: Synthetic construct: linc00340v15

<400> SEQUENCE: 15

atgagtgagg atcaatggga agaagagagc cagccaggaa gttgaagatt tgtccaggag     60

cagatagctg aagagagaga gagagaagag agaacggctt acagctcagg tcctctctcc    120

atgcttagga accactacaa atgctactgc cttgagtctc attttgtttc cctctggaaa    180

ccacatgtgt accttgtttg caacagtatg ggtatggatg ttttggcaaa aaaaaaaaaa    240


<210> SEQ ID NO 16
<211> LENGTH: 311
<212> TYPE: DNA
<213> ORGANISM: Artificial Sequence
<220> FEATURE:
<223> OTHER INFORMATION: Synthetic construct: linc00340v16

<400> SEQUENCE: 16

atgagtgagg atcaatggga agaagagagc cagccaggaa gttgaagatt tgtccaggag     60

cagatagctg aagagagaga gagagaagag agaacggctt acagctcagg tcctctctcc    120

atgcttagga accactacaa atgctactgc cttgagtctc attttgtttc cctctggaaa    180

ccacatgtgt accttgtttg caacagtatg ggtatggatg ttttggtagt tcttacacat    240

ttattttaaa atttaaagaa gtagtgccat aaagctttat caggatgtat ttaaaatgaa    300
```

aaaaaaaaaa a 311

<210> SEQ ID NO 17
<211> LENGTH: 451
<212> TYPE: DNA
<213> ORGANISM: Artificial Sequence
<220> FEATURE:
<223> OTHER INFORMATION: Synthetic construct: linc00340v17

<400> SEQUENCE: 17
atgagtgagg atcaatggga agaagagagc cagccaggaa gttgaagatt tgtccaggag 60
cagatagctg aagagagaga gagagaagag agaacggctt acagctcagg tcctctctcc 120
atgcttagga accactacaa atgctgctgc cttgagtctc attttgtttc cctctggaaa 180
ccacatgtgt accttgtttg caacagtatg ggtatggatg ttttggtagt tcttacacat 240
ttattttaaa atttaaagaa gtagtgccat aaagctttat caggatgtat ttaaaatgaa 300
aatagtctct tgttatctag catgcaactg attctttcaa tttggtttgg ttagtcagaa 360
tcttaccaga agtctgtcca ggtgataggt tagttgagag catcaagacc aaccaaaata 420
aaacaaaaac aatagccgaa aaaaaaaaaa a 451

<210> SEQ ID NO 18
<211> LENGTH: 100
<212> TYPE: DNA
<213> ORGANISM: Artificial Sequence
<220> FEATURE:
<223> OTHER INFORMATION: Synthetic construct: linc00340v18

<400> SEQUENCE: 18
atgagtgagg atcaatggga agaagagagc cagccagctc tgtattctaa gaacctggaa 60
acaatcttta ttcacaccgt taagaccaaa aaaaaaaaaa 100

<210> SEQ ID NO 19
<211> LENGTH: 43
<212> TYPE: DNA
<213> ORGANISM: Artificial Sequence
<220> FEATURE:
<223> OTHER INFORMATION: Synthetic construct: linc00340v

<400> SEQUENCE: 19
atgagtgagg atcaatggga agaagagagc caaaaaaaaa aaa 43

<210> SEQ ID NO 20
<211> LENGTH: 223
<212> TYPE: DNA
<213> ORGANISM: Artificial Sequence
<220> FEATURE:
<223> OTHER INFORMATION: Synthetic construct: linc00340v

<400> SEQUENCE: 20
ctgtgtctcc ttgcttctga ttctacatct ccatccatgg gccactgttt cagcaacctc 60
agccagtgca acacaacctc agccaagaag agtatgcaga gaaaggagtc ccctacctgc 120
cacaaaactg ttgtctgaaa actgtctcat attgtctcaa gttgtcattc attgtgaatt 180
agacctgttt aacatgtaat ctgcaacatg aaaaaaaaaa aaa 223

<210> SEQ ID NO 21
<211> LENGTH: 210
<212> TYPE: DNA
<213> ORGANISM: Artificial Sequence
<220> FEATURE:
<223> OTHER INFORMATION: Synthetic construct: linc00340v21

<400> SEQUENCE: 21

```
ctgtgtctcc ttgcttctga ttctacatct ccatccatgg gccactgttt cagcaacctc     60
agccagtgca acacaacctc agccaagaag agtatgcaga gaaaggagtc ccctacctgc    120
cacaaaactg ttgtctgaaa actgtctcat attgtctcaa gttgtcattc attgtgaatt    180
agacctgttt aacatggaaa aaaaaaaaaa                                     210
```

<210> SEQ ID NO 22
<211> LENGTH: 161
<212> TYPE: DNA
<213> ORGANISM: Artificial Sequence
<220> FEATURE:
<223> OTHER INFORMATION: Synthetic construct: linc00340v22

<400> SEQUENCE: 22

```
ctgtgtctcc ttgcttctga ttctacatct ccatccatgg gccactgttt cagcaacctc     60
agccagtgca acacaacctc agccaagaag agtatgcaga gaaaggagtc ccctacctgc    120
cacaaaactg ttgtctgaaa actgtctcaa aaaaaaaaaa a                        161
```

<210> SEQ ID NO 23
<211> LENGTH: 159
<212> TYPE: DNA
<213> ORGANISM: Artificial Sequence
<220> FEATURE:
<223> OTHER INFORMATION: Synthetic construct: linc00340v23

<400> SEQUENCE: 23

```
ctgtgtctcc ttgcttctga ttctacatct ccatccatgg gccactgttt cagcaacctc     60
agccagtgca acacaacctc agccaagaag agtatgcaga gaaaggagtc ccctacctgc    120
cacaaaactg ttgtctgaaa actgtcaaaa aaaaaaaaa                           159
```

<210> SEQ ID NO 24
<211> LENGTH: 717
<212> TYPE: DNA
<213> ORGANISM: Artificial Sequence
<220> FEATURE:
<223> OTHER INFORMATION: Synthetic construct: linc00340v24

<400> SEQUENCE: 24

```
tatagaaagc agcacacatg acctctgtcc ttccagctgc caccagtttc tgggttgtcg     60
agtgataccc tgaaagttta cagtcaacac tccttgtgtg gggtcagtcc tagaaatggc    120
gacgctgctc tccgaagata ggaaagaaga ggacctcatt ccattgagcc attgaccgaa    180
atattttctc aacaaagttg aactgagctg aaactgtgtg aatcatggca atacagtgaa    240
agacagtgat ttactgcttt tgagggcgtg catgtatatg attaacggat ggaagtgcag    300
gactccaaga tttacttcct tccctttcca gcagaattac ctgagacgag taaaatctac    360
tggtggagtc actccattat tcttatctgt ggagatctag atcttgattt gaaagtttct    420
gagaaaatct tcagctcaga cttgagggtc aactttacca gctgaaggat ctgcatttac    480
tgctcaacca catctaattt gatgtcctct gcagatttaa aatgtgtgcc ttcttttccg    540
tcaccaagtc atccctgggt tactactgaa catccttctc aattcccccc gacccatgga    600
tggctgttct ccattgtctg tttcaccaga tgtcctcaaa acaaacagac agaagaagga    660
agtggctaat ggagctgtgg agtccaagtg tgactgccaa gaggaatcca gcaaagc       717
```

<210> SEQ ID NO 25

<211> LENGTH: 500
<212> TYPE: DNA
<213> ORGANISM: Artificial Sequence
<220> FEATURE:
<223> OTHER INFORMATION: Synthetic construct: linc00340v25

<400> SEQUENCE: 25

```
acacatgacc tctgtccttc cagctgccac cagtttctgg gttgtcgagt gataccctga     60

aagtttacag tcaacactcc ttgtgtgggg tcagtcctag aaatggcgac gctgctctcc    120

gaagatagga aagaaaagga cctcattcca ttgagccatt gaccgaaata ttttctcaac    180

aaagttgaac tgagctgaaa ctgtgtgaat catggcaata cagtgaaaga cagtgattta    240

ctgcttttga gggcgtgcat gtatatgatt aacggatgga agtgcaggac tccaagattt    300

acttccttcc ctttccagca gaattacctg agacgagtaa aatctactgg tggagtcact    360

ccattattct tatctgtgga gatctagatc ttgatttgaa agtttctgag aaaatcttca    420

gctcagactt gagggtcaac tttaccagct gaaggagctg tggagtccaa gtgtgactgc    480

caagaggaat ccagcaaagc                                                500
```

<210> SEQ ID NO 26
<211> LENGTH: 290
<212> TYPE: DNA
<213> ORGANISM: Artificial Sequence
<220> FEATURE:
<223> OTHER INFORMATION: Synthetic construct: linc00340v26
<220> FEATURE:
<221> NAME/KEY: misc_feature
<222> LOCATION: (20)..(20)
<223> OTHER INFORMATION: n is a, c, g, or t

<400> SEQUENCE: 26

```
agtcctagaa atggcgacgn tgctctccga agataggaaa gaaaaggacc tcattccatt     60

gagccattga ccgaaatatt ttctcaacaa agttgaactg agctgaaact gtgtgaatca    120

tggcaataca gtgaaagaca gtgatttact gcttttgagg gcgtgcatgt atatgattaa    180

cggatggaag tgcaggactc caagatttac ttccttccct ttccagcaga attacctgag    240

acgagagctg tggagtccaa gtgtgactgc caagaggaat ccagcaaagc              290
```

<210> SEQ ID NO 27
<211> LENGTH: 1904
<212> TYPE: DNA
<213> ORGANISM: Homo sapiens
<220> FEATURE:
<221> NAME/KEY: misc_feature
<223> OTHER INFORMATION: Parent linc00340 transcript

<400> SEQUENCE: 27

```
gtctgctccg ggacttggaa caaaaggggg aactctgatg aactctcttt cctcccctct     60

cccccggacg ccggggtatc tccctctcgc aactttgccg ccccgacttt ctctgctgtc    120

aggccgggaa aaagtgtccg aacgcctcgt ggactgcagc gggggaaatg tcccttaaaa    180

gtgcgacgaa gtggggaaga aggtgtaatt actattatca gcatctagaa agcatcatga    240

atttgctgga gtacttccta gcactgacct ccttcattct gcgttgttct tactggatct    300

ttccatcagc caacaatatg gaagtaccaa tacaaggtca aatcattcct ggattcatct    360

ggagttgctt aaaagttaaa tcattggaat ttttgatgat accttttcta tatggattac    420

aatttgatcg ctgggaattc tccaccttaa agaagtaccc tcaggtgact acagatgtgt    480

taacacccag catgttccgg taggagactt tctggatggg gaagatttcc aggaattggc    540
```

-continued

```
aacaagctca tttcactggt gggtttgctg aagcattatc acaagacagt cagaatgact    600
gatgagtgct cttcaggtgt gaatcatggc aatacagtga aagacagtga tttactgctt    660
ttgagggcgt gcatgtatat gattaacgga tggaagtgca ggactccaag atttacttcc    720
ttccctttcc agcagaatta cctgagacga gtaaaatcta ctggtggagt cactccatta    780
ttcttatctg tggagatcta gatcttgatt tgaaagtttc tgagaaaatc ttcagctcag    840
acttgagggt caactttacc agctgaagga tctgcattta ctgctcaacc acatctaatt    900
tgatgtcctc tgcagattta aaatgtgtgc cttctcttcc gtcaccaagt catccctggg    960
ttactactga acatccttct caattccccc cgacccatgg atggctgttc tccattgtct   1020
gtttcaccag atgtcctcaa aacaaacaga cagaagaagg aagtggctaa tggagctgtg   1080
gagtccaagt gtgactgcca agaggaatcc agcaaagcca aaaagcccaa gcatgtagcc   1140
ctgcccgaag cacgccacac gcatggaaaa cccagaggaa atgagtgagg atcaatggga   1200
agaagagagc cagccaggaa gttgaagatt tgtccaggag cagatagctg aagagagaga   1260
gagagaagag agaacggctt acagctcagg tcctctctcc atgcttagga accactacaa   1320
atgctactgc cttgagtctc attttgtttc cctctggaaa ccacatgtgt accttgtttg   1380
caacagtatg ggctcacagg cagaaggaat tttccttgtc ttggatgaga cttttgactt   1440
ggacttttgg gttaagttct ggagaccaga aggccaaaat caaaagtatg ggcaggcttg   1500
atttctttag aagactccag cggagaactg tgtctccttg cttctgattc tacatctcca   1560
tccatgggcc actgtttcag caacctcagc cagtgcaaca caacctcagc caagaagagt   1620
atgcagagaa aggagtcccc tacctgccac aaaactgttg tctgaaaact gtctcatatt   1680
gtctcaagtt gtcattcatt gtgaattaga cctgtttaac atgtaatctg caacatgctt   1740
cactgtctaa ttttccagag cccctcatat aaggaactgt attattggta taatcatcat   1800
ggtgaagaag ttggtatgtg ggggagagat gacagaaaca gagagtaagt cagagctggc   1860
tgcctgacag ataaaaagga aatgaccaaa aaaaaaaaaa aaaa                     1904
```